United States Patent
Ishihara et al.

(10) Patent No.: US 10,588,581 B2
(45) Date of Patent: Mar. 17, 2020

(54) CROSS-SECTIONAL IMAGE GENERATING APPARATUS, CROSS-SECTIONAL IMAGE GENERATING METHOD, AND RECORDING MEDIUM

(71) Applicant: FUJITSU LIMITED, Kawasaki-shi, Kanagawa (JP)

(72) Inventors: Masaki Ishihara, Kawasaki (JP); Susumu Endo, Kawasaki (JP); Masahiko Sugimura, Kawasaki (JP); Hiroaki Takebe, Kawasaki (JP); Takayuki Baba, Kawasaki (JP); Yusuke Uehara, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 117 days.

(21) Appl. No.: 15/908,238

(22) Filed: Feb. 28, 2018

(65) Prior Publication Data

US 2018/0184987 A1    Jul. 5, 2018

Related U.S. Application Data

(63) Continuation of application No. PCT/JP2015/075004, filed on Sep. 2, 2015.

(51) Int. Cl.
*G06K 9/00* (2006.01)
*A61B 6/03* (2006.01)
(Continued)

(52) U.S. Cl.
CPC .......... *A61B 6/03* (2013.01); *A61B 5/05* (2013.01); *A61B 6/032* (2013.01); *A61B 6/5205* (2013.01);
(Continued)

(58) Field of Classification Search
None
See application file for complete search history.

(56) References Cited

U.S. PATENT DOCUMENTS 8,867,807 B1 * 10/2014 Fram ............... G06F 19/321
                                            382/128
9,454,643 B2 * 9/2016 Hu ..................... G06T 19/20
(Continued)

FOREIGN PATENT DOCUMENTS

JP    2002-245487    8/2002
JP    2004-73379     3/2004
(Continued)

OTHER PUBLICATIONS

Japanese Patent Office Action dated Mar. 12, 2019 in Application No. 2017-537149.
(Continued)

*Primary Examiner* — Soo Jin Park
(74) *Attorney, Agent, or Firm* — Staas & Halsey LLP

(57) ABSTRACT

A non-transitory computer-readable recording medium storing an image interpretation support program that causes a computer to execute a process, the process including generating first data indicating a first internal structure of a predetermined object, based on a first cross-sectional image group acquired with respect to the predetermined object; detecting a structural change of the first internal structure from a second internal structure of the predetermined object, based on second data indicating the second internal structure and the generated first data, the second data being generated based on a second cross-sectional image group acquired at a past time; identifying a new cross-section with respect to the predetermined object based on the structural change; generating a cross-sectional image of the predetermined object with respect to the new cross-section, based on the first cross-sectional image group; and displaying the gener-
(Continued)

ated cross-sectional image together with first information indicating the detected structural change.

9 Claims, 26 Drawing Sheets

(51) Int. Cl.
*G06T 7/30* (2017.01)
*A61B 6/00* (2006.01)
*G06T 19/00* (2011.01)
*A61B 5/05* (2006.01)

(52) U.S. Cl.
CPC .............. *G06T 7/30* (2017.01); *G06T 19/00* (2013.01); *G06T 2207/10081* (2013.01); *G06T 2207/20012* (2013.01); *G06T 2207/30064* (2013.01); *G06T 2210/41* (2013.01); *G06T 2219/008* (2013.01)

(56) References Cited

U.S. PATENT DOCUMENTS

| | | | |
|---|---|---|---|
| 9,747,688 B2* | 8/2017 | Hu | G06T 7/174 |
| 10,127,662 B1* | 11/2018 | Reicher | G06F 16/583 |
| 2004/0059214 A1 | 3/2004 | Tomoda et al. | |
| 2007/0242901 A1 | 10/2007 | Huang et al. | |
| 2007/0286469 A1 | 12/2007 | Yamagata et al. | |
| 2008/0170771 A1 | 7/2008 | Yamagata et al. | |
| 2008/0253631 A1* | 10/2008 | Oosawa | G16H 15/00 382/128 |
| 2012/0250966 A1* | 10/2012 | Fujisawa | G06T 7/0016 382/131 |
| 2013/0182925 A1 | 7/2013 | Razeto et al. | |

FOREIGN PATENT DOCUMENTS

| | | |
|---|---|---|
| JP | 2005-329099 | 12/2005 |
| JP | 2007-283108 | 11/2007 |
| JP | 2008-12291 | 1/2008 |
| JP | 2008-194456 | 8/2008 |
| JP | 2008-259622 | 10/2008 |
| JP | 2009-160045 | 7/2009 |
| JP | 2012-213604 | 11/2012 |
| JP | 2013-141603 | 7/2013 |

OTHER PUBLICATIONS

Japanese Patent Office English Abstract for Japanese Patent Publication No. 2002-245487, published Aug. 30, 2002.
Japanese Patent Office English Abstract for Japanese Patent Publication No. 2005-329099, published Dec. 2, 2005.
Japanese Patent Office English Abstract for Japanese Patent Publication No. 2008-12291, published Jan. 24, 2008.
Japanese Patent Office English Abstract for Japanese Patent Publication No. 2007-283108, published Nov. 1, 2007.
Japanese Patent Office English Abstract for Japanese Patent Publication No. 2013-141603, published Jul. 22, 2013.
Espacenet English Abstract for Japanese Patent Publication No. 2008-259622, published Oct. 30, 2008.
Espacenet English Abstract for Japanese Patent Publication No. 2012-213604, published Nov. 8, 2012.
Espacenet English Abstract for Japanese Patent Publication No. 2009-160045, published Jul. 23, 2009.
Espacenet English Abstract for Japanese Patent Publication No. 2008-194456, published Aug. 28, 2008.
Written Opinion of the International Searching Authority dated Nov. 24, 2015 in corresponding International Patent Application No. PCT/JP2015/075004.
International Search Report dated Nov. 24, 2015 in corresponding International Patent Application No. PCT/JP2015/075004.
Kitaoka et al., "Simulations of Bronchial Displacement Owing to Solitary Pulmonary Nodules", Osaka University Knowledge Archive, Nippon Acta Radiologica, 59(7), Jun. 25, 1999, pp. 318-324 and Bibliographic pp. 1-2.
Japanese Patent Office English Abstract for Japanese Patent Publication No. 2004-73379, published Mar. 11, 2004.
Japanese Patent Office Action dated Oct. 1, 2019 in Application No. 2017-537149.

* cited by examiner

FIG.5

| PATIENT ID: xxx | | |
|---|---|---|
| CAPTURED DATE AND TIME | 2014.2.5 | 2014.8.3 |
| CAPTURED REGION | LUNG | LUNG |
| NAME OF SERIES | SERIES A | SERIES B |
| CROSS-SECTIONAL IMAGE GROUP | ImageA001<br>ImageA002<br>ImageA003<br>⋮<br>ImageA015<br>ImageA016<br>ImageA017<br>ImageA018<br>⋮<br>ImageA030 | ImageB001<br>ImageB002<br>ImageB003<br>⋮<br>ImageB015<br>ImageB016<br>ImageB017<br>ImageB018<br>⋮<br>ImageB030 |

FIG.6
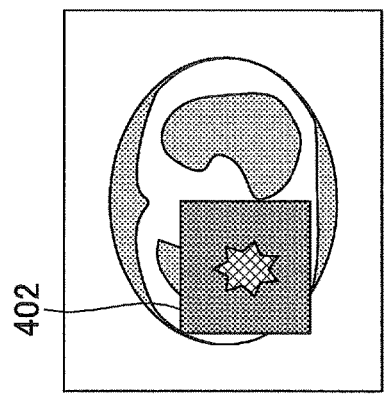
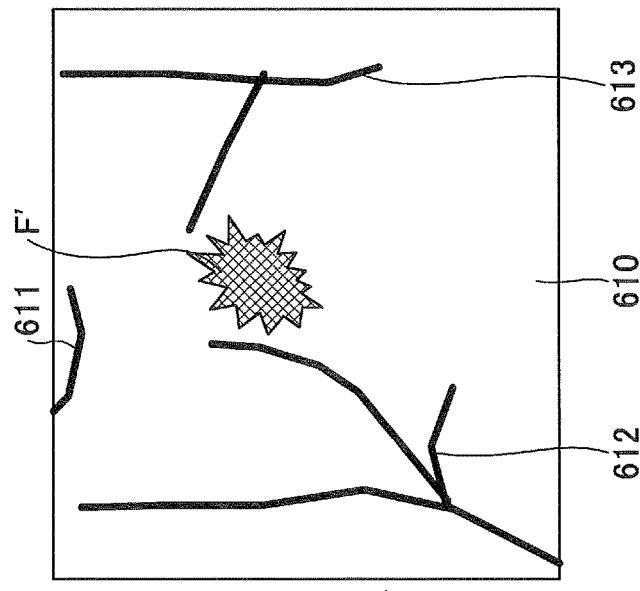
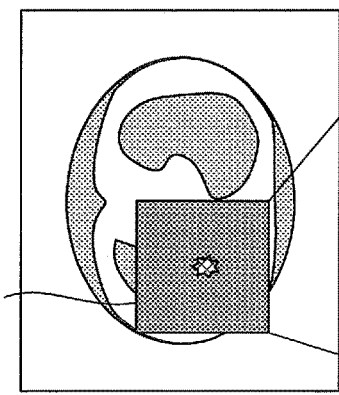
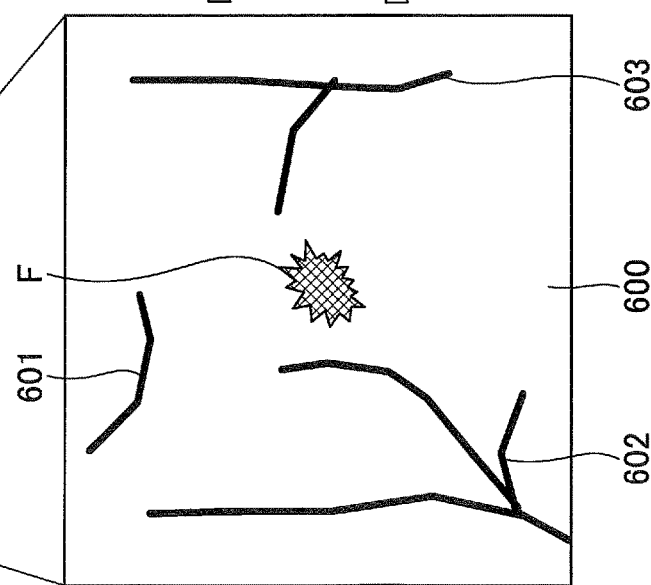

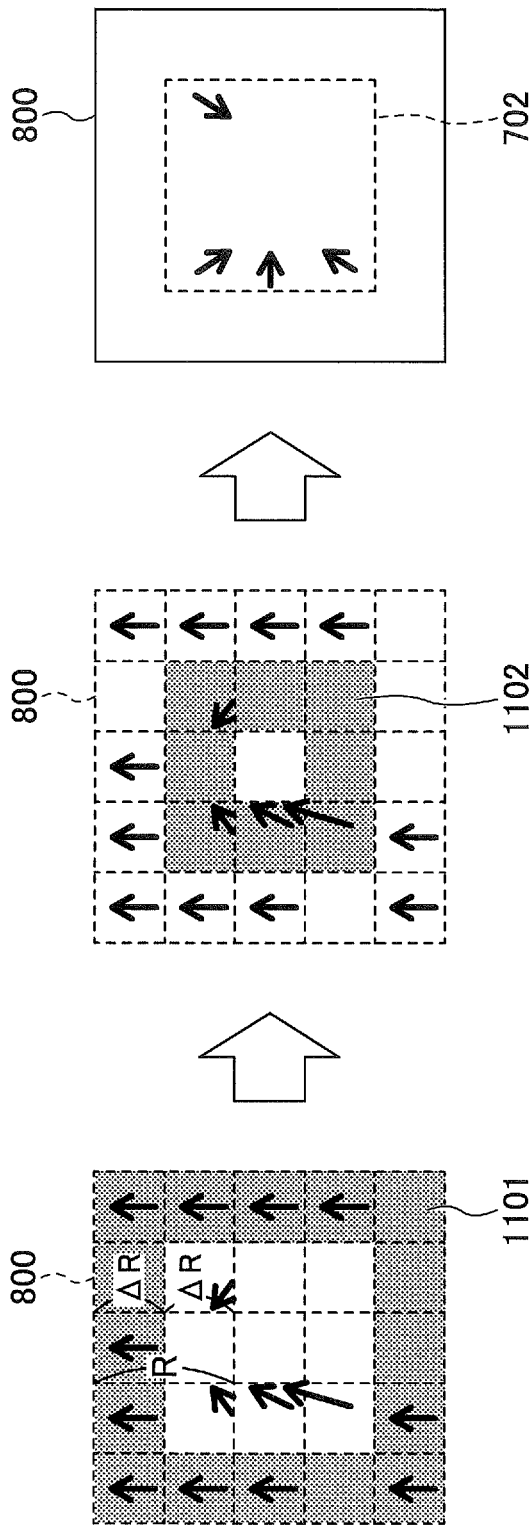

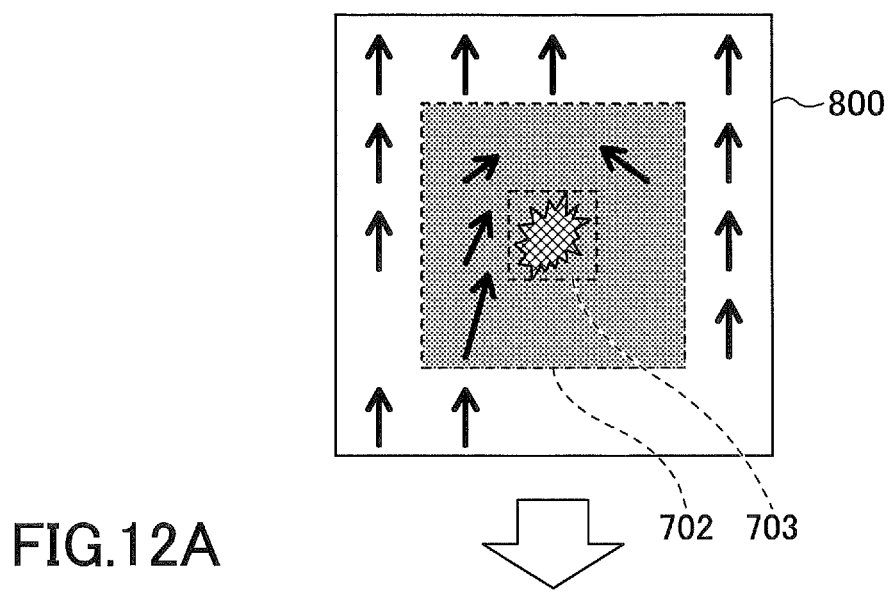
FIG.12A
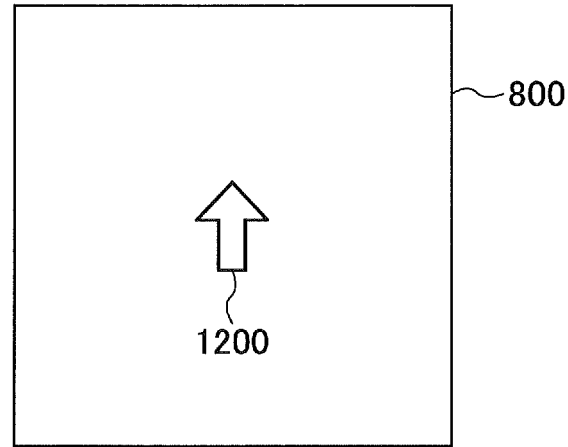
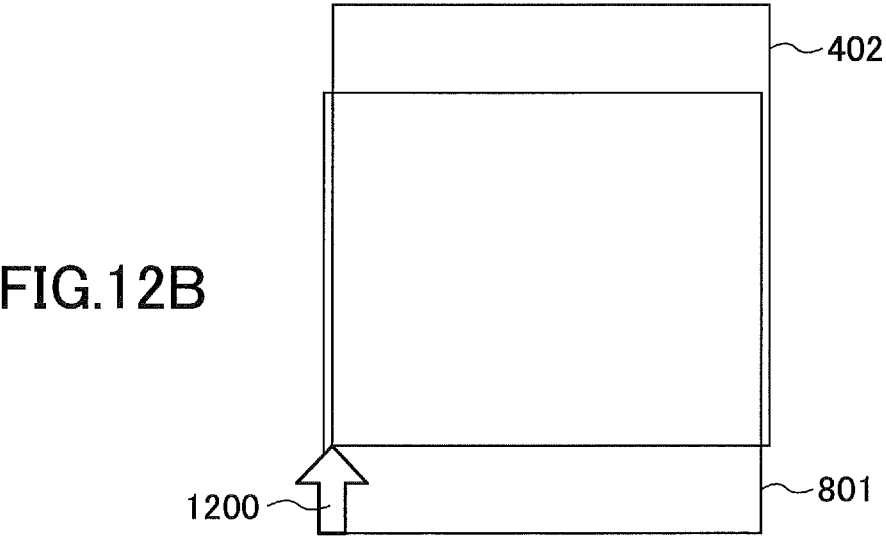
FIG.12B

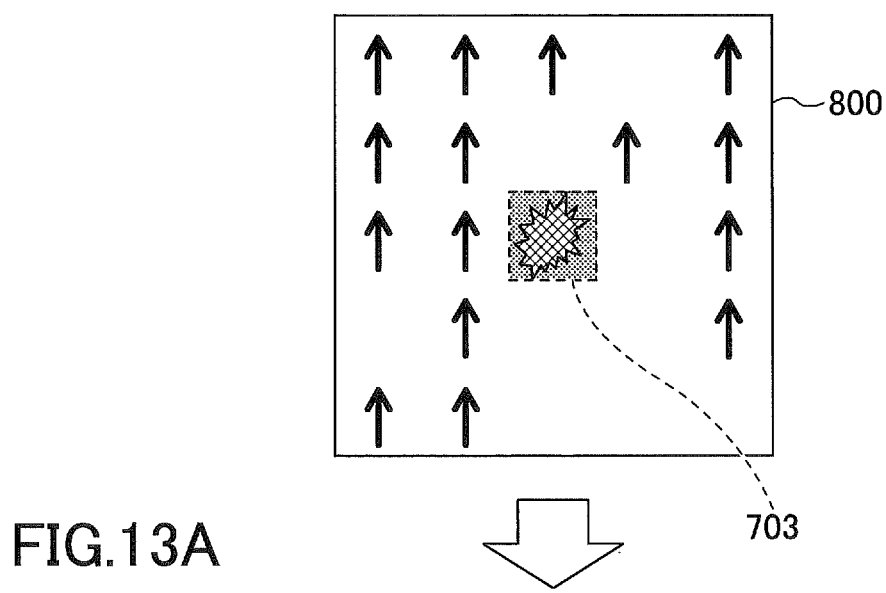
FIG.13A
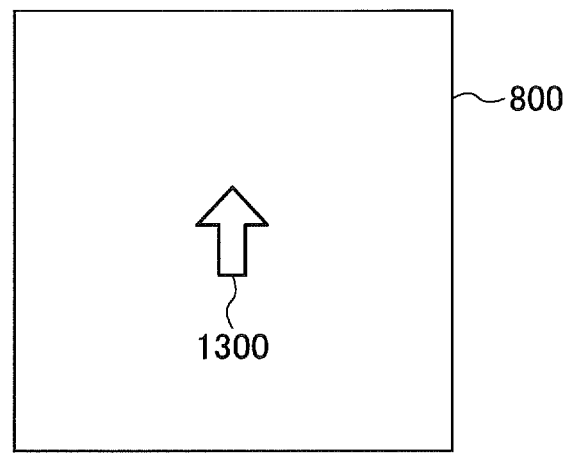
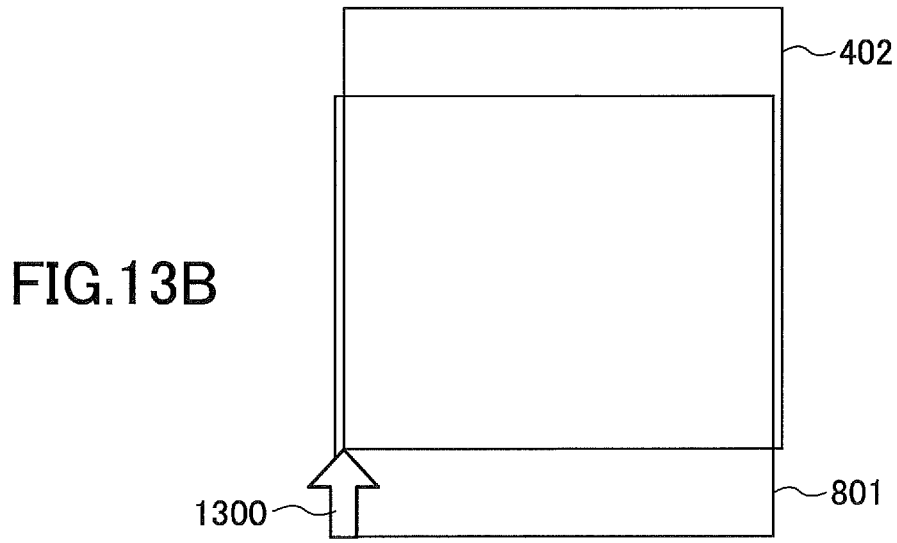
FIG.13B

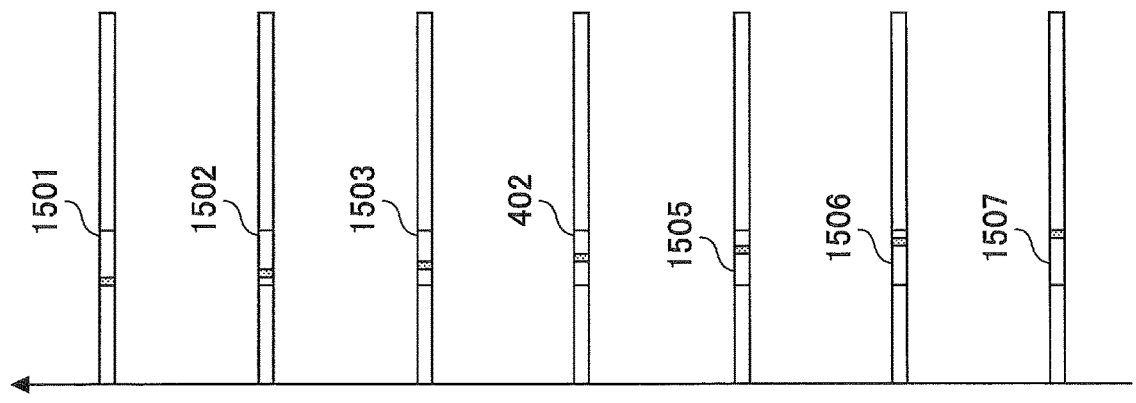
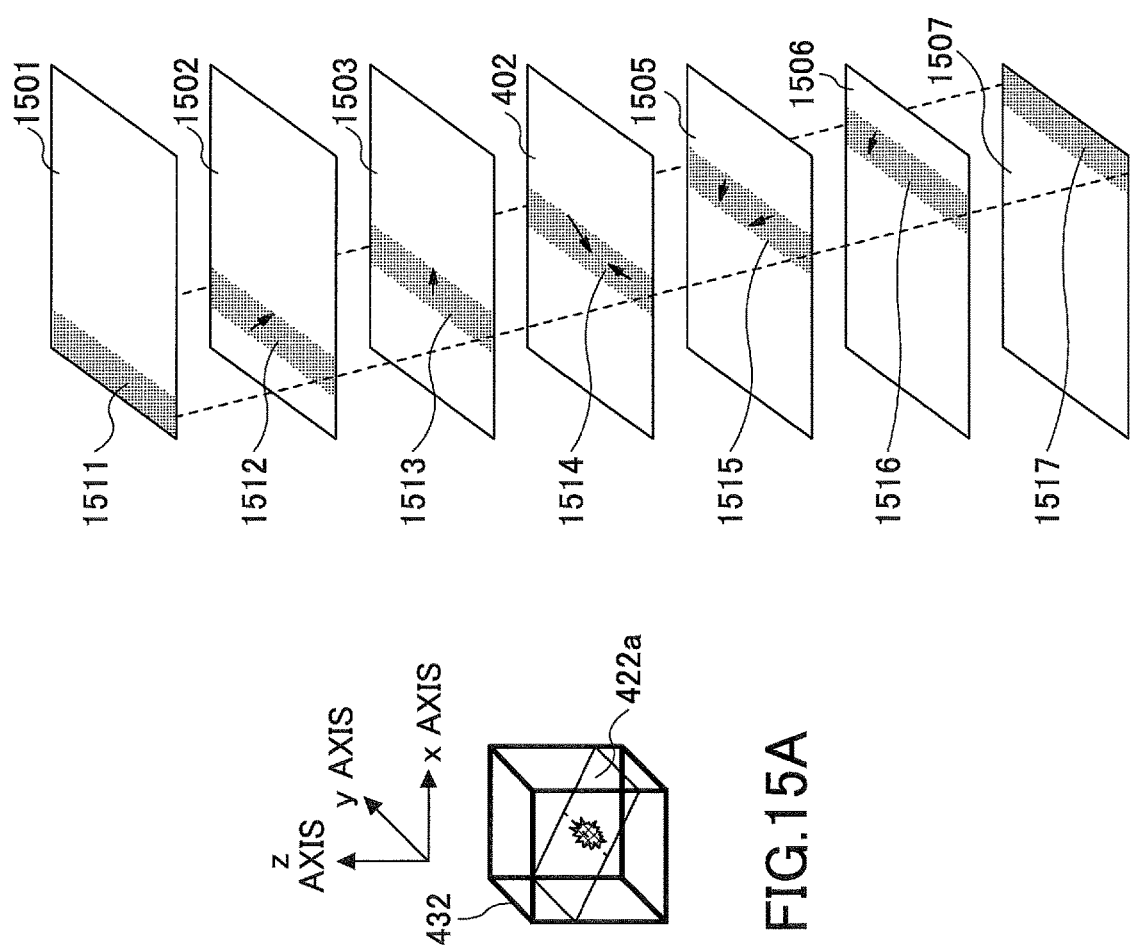

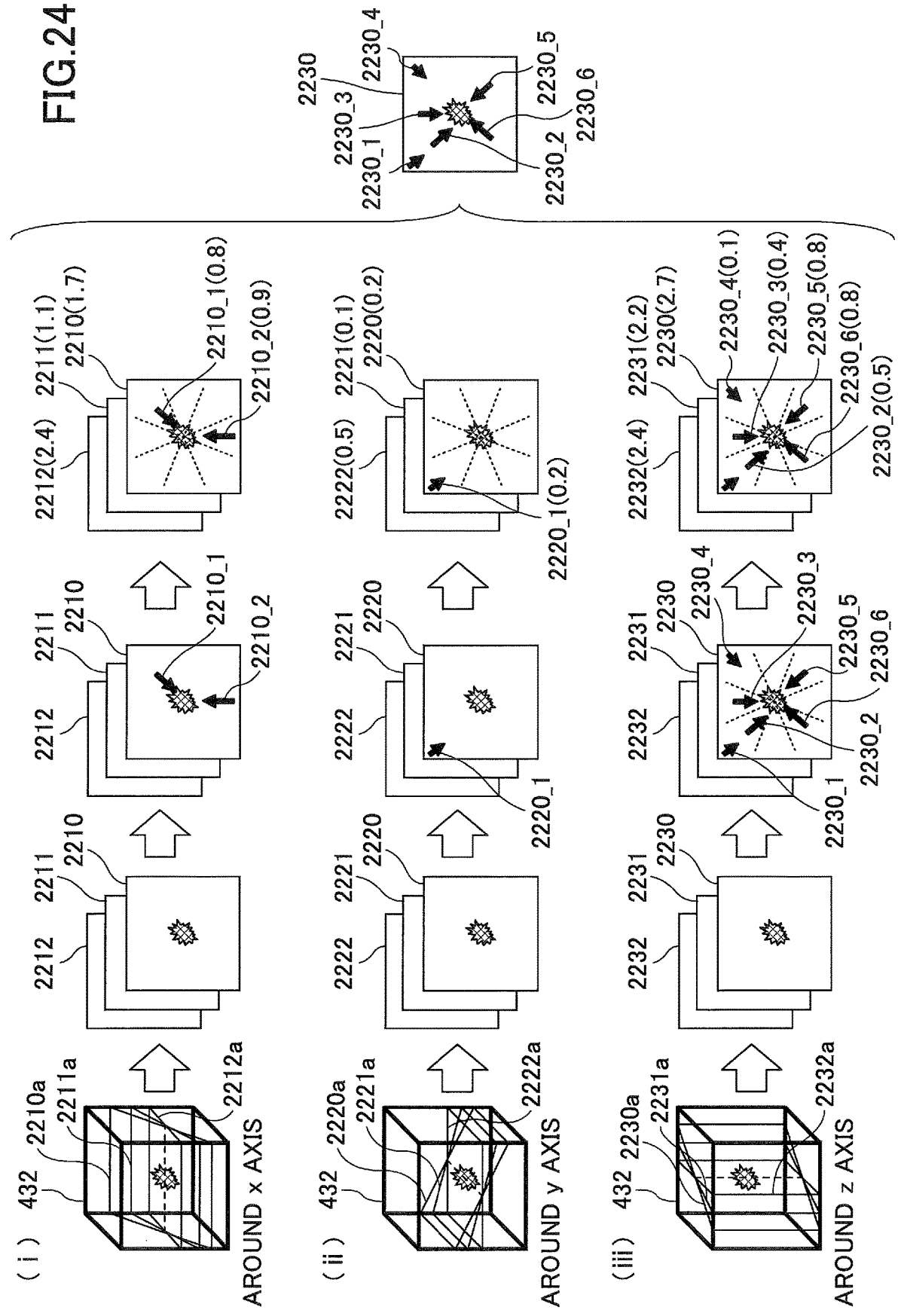

CROSS-SECTIONAL IMAGE GENERATING APPARATUS, CROSS-SECTIONAL IMAGE GENERATING METHOD, AND RECORDING MEDIUM

CROSS-REFERENCE TO RELATED APPLICATION

This application is a U.S. continuation application filed under 35 USC 111(a) claiming benefit under 35 USC 120 and 365(c) of PCT Application PCT/JP2015/075004 filed on Sep. 2, 2015, the entire contents of which are incorporated herein by reference.

FIELD

The embodiments discussed herein are related to a cross-sectional image generating apparatus, a cross-sectional image generating method, and a recording medium.

BACKGROUND

In the medical field, diagnostic image interpretation is performed to determine a patient's illness, by using CT (Computed Tomography) images captured at different time periods, and comparing the images of a diseased portion or a portion suspected to be diseased, by a radiographic image interpreting doctor, etc.

Patent Document 1: Japanese Laid-Open Patent Publication No. 2013-141603

In the case of a patient having a tumor (for example, an adenocarcinoma) in the lung, there is a characteristic of the alveoli collapsing due to the tumor, and accordingly, the positions of the surrounding tissue, such as blood vessels, shifting in position, so as to converge around the collapsed position. Additionally, a lung varies in shape (deforms) due to the influence of the patient's respiration and heartbeat. Therefore, unless the image interpreting doctor is highly experienced, it is difficult to find the convergence around the tumor based on a CT image obtained by capturing an image of the lung and determine that the tumor is an adenocarcinoma.

SUMMARY

According to an aspect of the embodiments, a non-transitory computer-readable recording medium stores an image interpretation support program that causes a computer to execute a process, the process including generating first data indicating a first internal structure of a predetermined object, based on a first cross-sectional image group acquired with respect to the predetermined object; detecting a structural change of the first internal structure from a second internal structure of the predetermined object, based on second data indicating the second internal structure and the generated first data indicating the first internal structure, the second data being generated based on a second cross-sectional image group acquired at a past time with respect to the predetermined object; identifying a new cross-section with respect to the predetermined object based on the detected structural change; generating a cross-sectional image of the predetermined object with respect to the new cross-section, based on the first cross-sectional image group; and displaying the generated cross-sectional image together with first information indicating the detected structural change.

The object and advantages of the invention will be realized and attained by means of the elements and combinations particularly pointed out in the appended claims. It is to be understood that both the foregoing general description and the following detailed description are exemplary and explanatory and are not restrictive of the invention as claimed.

BRIEF DESCRIPTION OF THE DRAWINGS

FIG. 5 is a diagram illustrating an example of information stored in an image DB;

FIG. 6 is a diagram illustrating factors of local positional variations in a comparison target CT image with respect to a comparison source CT image;

FIG. 11 is a diagram illustrating the contents of processes executed by a convergence area determining unit;

FIGS. 12A and 12B are diagrams illustrating a method of calculating a representative vector in a case where it is determined that there is a convergence area;

FIGS. 13A and 13B are diagrams illustrating a method of calculating the representative vector in a case where it is determined that there is no convergence area;

FIGS. 15A through 15C are diagrams illustrating contents of processes by a partial image extracting unit according to a first embodiment;

FIG. 24 is a diagram illustrating contents of processes by the cross-sectional image generating unit according to the second embodiment;

DESCRIPTION OF EMBODIMENTS

Figure 1:
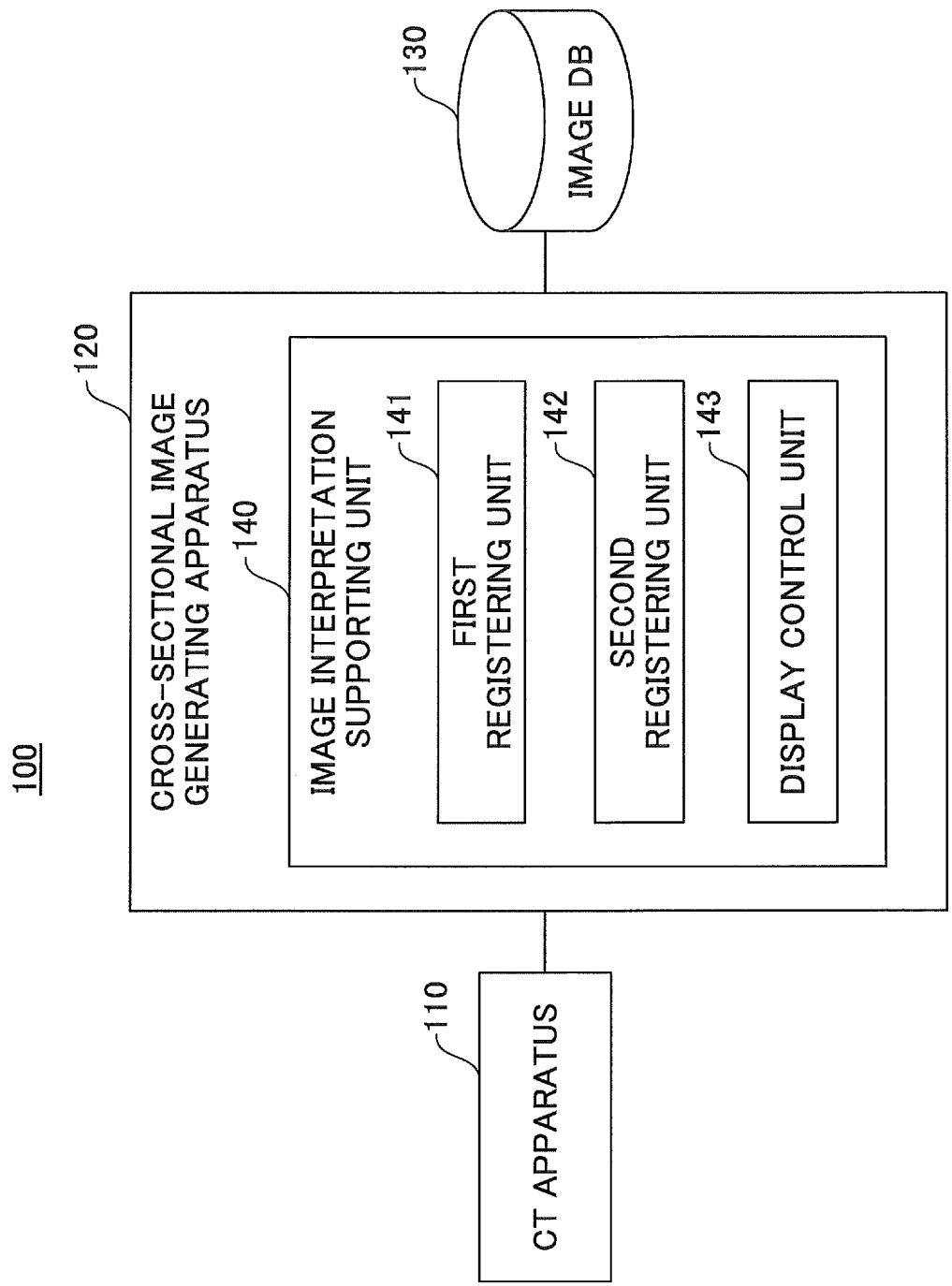
FIG. 1 is a diagram illustrating an example of a CT image capturing system.

Preferred embodiments of the present invention will be explained with reference to accompanying drawings. Note that in the present specification and the drawings, the same reference numerals are given to constituent elements having substantially the same functional configuration, and redundant descriptions will be omitted.

First Embodiment

First, a CT (Computed Tomography) image capturing system including a cross-sectional image generating apparatus according to a first embodiment will be described. FIG. 1 is a diagram illustrating an example of a CT image capturing system.

A CT image capturing system 100 includes a CT apparatus 110, a cross-sectional image generating apparatus 120, and an image database (hereinafter, the database is abbreviated as "DB") 130. The CT apparatus 110 and the cross-sectional image generating apparatus 120 are electrically connected to each other, and various kinds of data are transmitted and received between these apparatuses. Furthermore, the cross-sectional image generating apparatus 120 and the image DB 130 are also electrically connected, and various kinds of data are also transmitted and received between the two devices.

The CT apparatus 110 scans the inside of a patient's body by using radiation, etc., and performs processing by using a computer to generate a CT image that is a cross-sectional image of the cross-section (reference cross-section) obtained by disc-shaped partitioning of the patient (hereinafter, such a process is referred to as "capturing a CT image"). The CT apparatus 110 transmits the captured CT image to the cross-sectional image generating apparatus 120.

The cross-sectional image generating apparatus 120 stores the CT image captured by the CT apparatus 110, in the connected image DB 130. Furthermore, the cross-sectional image generating apparatus 120 processes the CT image captured by the CT apparatus 110 and displays the processed image to a radiographic image interpreting doctor, etc. (hereinafter, simply referred to as an "image interpreting doctor"). At this time, based on instructions from the image interpreting doctor, the cross-sectional image generating apparatus 120 generates and displays a cross-sectional image of a cross-section that is different from the cross-section used for generating the CT image above.

Note that the cross-sectional image generating apparatus 120 includes an image interpretation support program installed therein, and by executing the image interpretation support program by a computer, the cross-sectional image generating apparatus 120 functions as an image interpretation supporting unit 140, and executes processes.

The image DB 130 receives CT images captured by the CT apparatus 110 via the cross-sectional image generating apparatus 120 and separately stores groups of CT images that have been captured at the same time (cross-sectional image groups with respect to the reference cross-section).

The image interpretation supporting unit 140 is a function used when the image interpreting doctor performs interpretation of the CT image stored in the image DB 130. For example, the image interpretation supporting unit 140 displays CT images captured at different time periods in parallel, so that the image interpreting doctor can interpret the images while comparing the images. Note that in the following description, one of the CT images displayed in parallel (for example, a past CT image captured before the elapse of a predetermined time period) is referred to as a "comparison source CT image", and another one of the CT images (for example, a most recent CT image captured after the predetermined time period has elapsed) is referred to as a "comparison target CT image".

The image interpretation supporting unit 140 enlarges and displays an image of a predetermined area (ROI: region of interest) including a position specified by the image interpreting doctor in the comparison source CT image, on an enlarged display screen. Furthermore, the image interpretation supporting unit 140 extracts an image of a corresponding area, which corresponds to the predetermined area in the comparison source CT image including the specified position, from the comparison target CT image, and enlarges and displays the extracted image on an enlarged display screen. In this manner, the image interpretation supporting unit 140 automatically enlarges and displays an image of a predetermined area including the specified position, and an image of the corresponding area. Thus, for the image interpreting doctor, the burden of image interpretation can be reduced, and the time and labor of operations for enlarging and displaying images can be saved.

Note that in order to execute these processes, the image interpretation supporting unit 140 includes a first registering unit 141, a second registering unit 142, and a display control unit 143.

The first registering unit 141 is implemented, for example, by executing a first registration program by a computer. When the CT images captured at different time periods are displayed in parallel, the first registering unit 141 corrects the positional deviation between the CT images by affine transformation, so as to perform global positional alignment between the CT images.

The second registering unit 142 is implemented, for example, by executing a second registration program by a computer. When an image of the predetermined area including the position specified by the image interpreting doctor is enlarged and displayed, the second registering unit 142 performs a conversion process on the comparison target CT image to perform local positional alignment, and extracts the image of the corresponding area from the comparison target CT image. Note that the conversion process may include various processes; however, in the first embodiment, the conversion process refers to parallel movement, and the image of the corresponding area extracted from the comparison target CT image upon performing the conversion process, is referred to as an "image subjected to local positional alignment".

Furthermore, in response to an instruction to change the cross-section from the image interpreting doctor, the second registering unit 142 performs a "cross-section changing process" of generating a cross-sectional image of a cross-section that is different from the reference cross-section, so that the image interpreting doctor can properly perform image interpretation with respect to a tumor.

The display control unit 143 is implemented, for example, by executing a display program by a computer. The display control unit 143 displays the comparison source CT image selected by the image interpreting doctor and enlarges and displays the image of a predetermined area including the position specified by the image interpreting doctor, on an enlarged display screen. Furthermore, the display control unit 143 enlarges and displays an image subjected to local positional alignment, which is extracted by the second registering unit 142, on the enlarged display screen. Furthermore, in the case where the second registering unit 142 has performed the cross-section changing process, the display control unit 143 enlarges and displays a cross-sectional image generated in the cross-section changing process, on the enlarged display screen.

Figure 2:
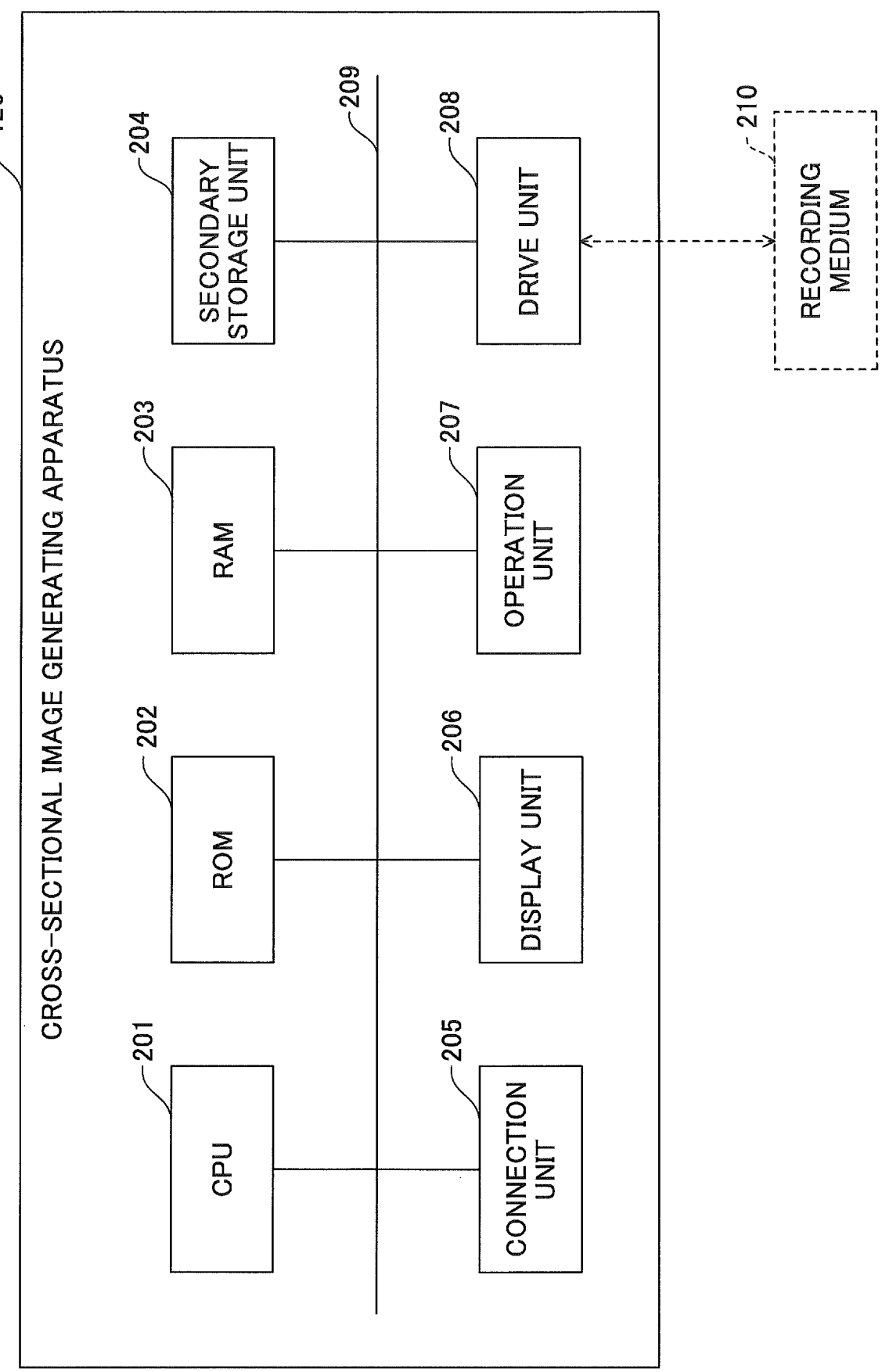
FIG. 2 is a hardware block diagram of a cross-sectional image generating apparatus.

Next, a hardware configuration of the cross-sectional image generating apparatus 120 will be described. FIG. 2 is a hardware block diagram of the cross-sectional image generating apparatus 120. As illustrated in FIG. 2, the cross-sectional image generating apparatus 120 includes a CPU (Central Processing Unit) 201, a ROM (Read-Only Memory) 202, and a RAM (Random Access Memory) 203. Furthermore, the cross-sectional image generating apparatus 120 includes a secondary storage unit 204, a connection unit 205, a display unit 206, an operation unit 207, and a drive unit 208. Note that the respective units of the cross-sectional image generating apparatus 120 are mutually connected via a bus 209.

The CPU 201 is a computer that executes various programs (for example, the first registration program, the second registration program, and the display program, etc.) stored in the secondary storage unit 204.

The ROM 202 is a nonvolatile memory. The ROM 202 functions as a main storage unit that stores various programs and data, etc., used by the CPU 201 to execute various programs stored in the secondary storage unit 204. More specifically, the ROM 202 stores a boot program such as BIOS (Basic Input/Output System) or EFI (Extensible Firmware Interface).

The RAM 203 is a volatile memory, and includes a DRAM (Dynamic Random Access Memory) and a SRAM (Static Random Access Memory), etc. The RAM 203 is a main storage unit that provides a work area to be expanded when various programs stored in the secondary storage unit 204 are executed by the CPU 201.

The secondary storage unit 204 is a computer-readable storage device that records various programs installed in the cross-sectional image generating apparatus 120 and data generated by executing various programs, etc.

The connection unit 205 is connected to the CT apparatus 110 and the image DB 130, and performs transmission and reception of various kinds of data between the CT apparatus 110 and the image DB 130. The display unit 206 displays the CT images stored in the image DB 130 on a parallel display screen. The operation unit 207 accepts various operations on the cross-sectional image generating apparatus 120 performed by the image interpreting doctor.

The drive unit 208 is a device for setting a recording medium 210. The recording medium 210 includes a medium that optically, electrically or magnetically records information, such as a CD-ROM, a flexible disk, and a magneto-optical disk, etc. Furthermore, the recording medium 210 also includes a semiconductor memory, etc., for electrically recording information, such as ROM and a flash memory, etc.

Note that various programs stored in the secondary storage unit 204 are installed, for example, by setting the distributed recording medium 210 in the drive unit 208 and reading various programs recorded in the recording medium 210 by the drive unit 208. Alternatively, a program is installed by being downloaded from a network via the connection unit 205.

Next, a description is given of the relationship between the contents of processes by the image interpretation supporting unit 140 of the cross-sectional image generating apparatus 120, the contents of operations by the image interpreting doctor when the processes are executed by the image interpretation supporting unit 140, and a parallel display screen displayed on the display unit 206 of the cross-sectional image generating apparatus 120.

Figure 3:
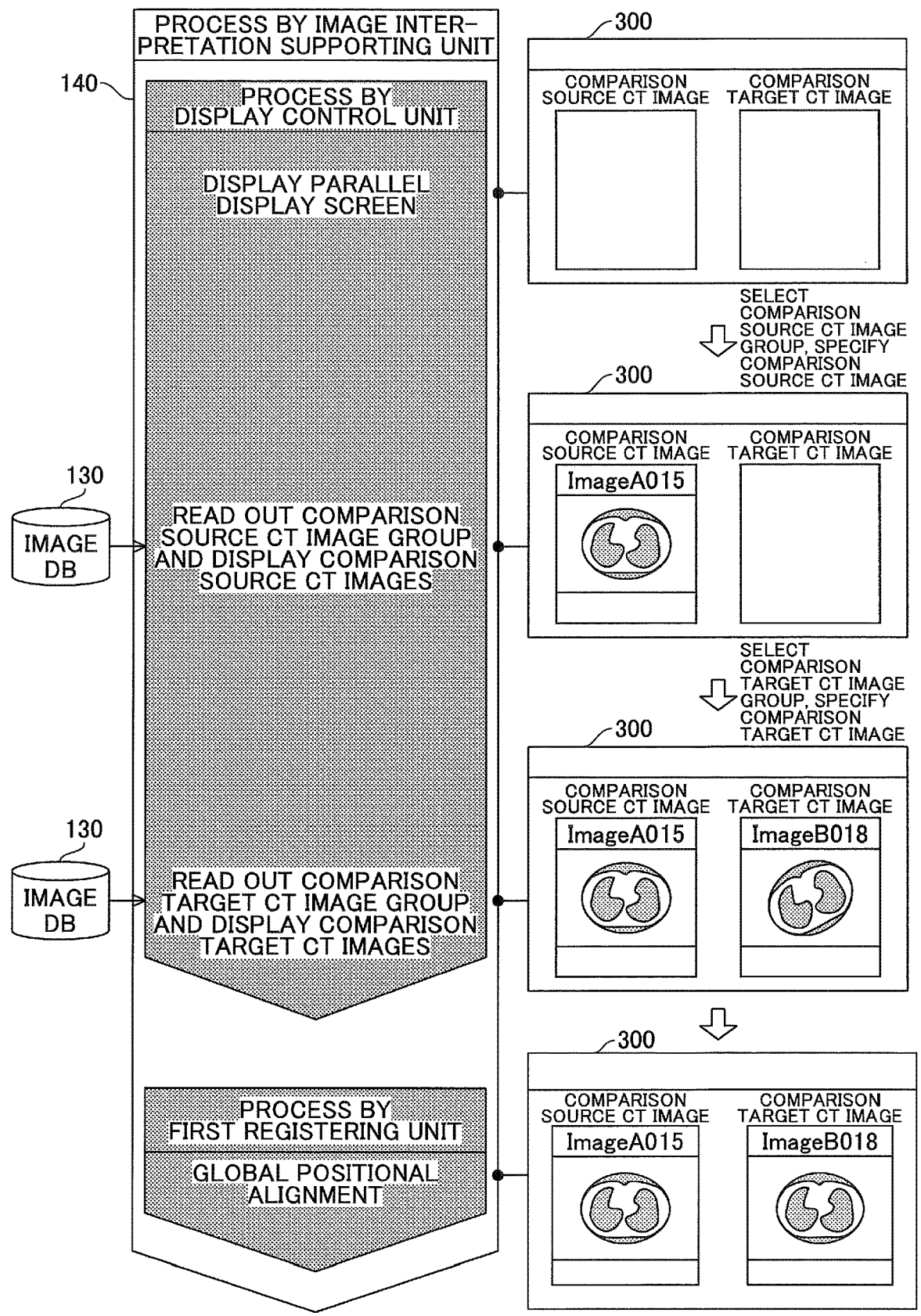
FIG. 3 is a diagram (part 1) illustrating the relationship between the contents of processes by an image interpretation supporting unit in the cross-sectional image generating apparatus, the contents of operations by the image interpreting doctor, and the display contents of a parallel display screen.
Figure 4:
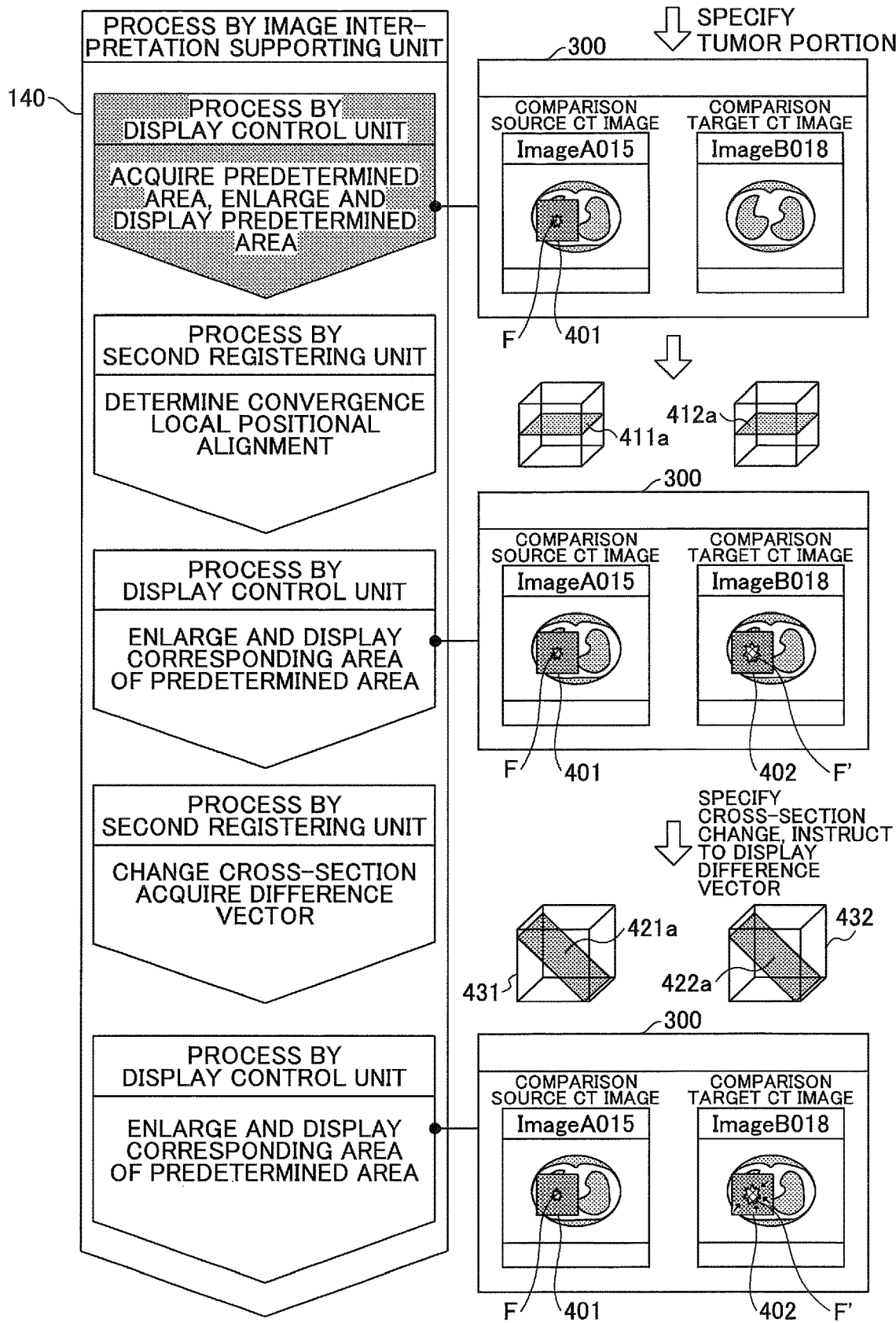
FIG. 4 is a diagram (part 2) illustrating the relationship between the contents of processes by an image interpretation supporting unit in the cross-sectional image generating apparatus, the contents of operations by the image interpreting doctor, and the display contents of a parallel display screen.

FIGS. 3 and 4 are diagrams (part 1 and part 2) illustrating the relationship between the contents of processes by the image interpretation supporting unit 140 in the cross-sectional image generating apparatus 120, the contents of operations by the image interpreting doctor, and the display contents of the parallel display screen.

When the image interpretation supporting unit 140 is activated in the cross-sectional image generating apparatus 120, a process by the display control unit 143 is started, and a parallel display screen 300 for displaying CT images captured at different time periods in parallel is displayed on the display unit 206, as illustrated in FIG. 3. In the parallel display screen 300, there is provided a function for the image interpreting doctor to select a cross-sectional image group of a predetermined region (here, the lung) captured at a predetermined time with respect to a predetermined patient, as a comparison source CT image group.

The display control unit 143 reads the comparison source CT image group selected by the image interpreting doctor, from the image DB 130. Furthermore, when the image interpreting doctor specifies a predetermined comparison source CT image (file name="ImageA015" in this case) in the selected comparison source CT image group, the display control unit 143 displays the specified comparison source CT image on the parallel display screen 300.

On the parallel display screen 300, there is provided a function for the image interpreting doctor to select, as a comparison target CT image group, a cross-sectional image group of the same region of the same patient captured at a different time, to be compared with the comparison source CT image. More specifically, there is provided a function for making the selection by inputting a patient ID, a captured date and time, and a captured region (in this case, the lung), etc.

The display control unit 143 reads, as a comparison target CT image group, a cross-sectional image group identified by the input patient name, captured date and time, and captured region, etc., from the image DB 130. Furthermore, the display control unit 143 reads the comparison target CT image (here, file name="ImageB018") specified by the image interpreting doctor from the read comparison target CT image group, and displays the specified comparison target CT image on the parallel display screen 300.

At this time, the first registering unit 141 of the image interpretation supporting unit 140 functions, and performs global positional alignment on the CT images that have been read, by making corrections by using affine transformation such as rotation and parallel movement. As global positional alignment is performed on all of the CT images, a global positional deviation between the comparison source CT image and the comparison target CT image is resolved.

When the global positional alignment is completed, on the parallel display screen, the image interpreting doctor can specify the position of a tumor portion F in the displayed comparison source CT image. On the parallel display screen, when the image interpreting doctor specifies the position of the tumor portion F, as illustrated in FIG. 4, the display control unit 143 enlarges and displays a predetermined area (ROI: region of interest) 401 including the position of the specified tumor portion F in an enlarged display screen on the comparison source CT image.

When the image of the predetermined area 401 is enlarged and displayed, the second registering unit 142 performs local positional alignment with respect to the corresponding area in the comparison target CT image. Accordingly, the second registering unit 142 extracts an image of the corresponding area (the image subjected to local positional alignment) including the position of the tumor portion corresponding to the tumor portion F. Note that the second registering unit 142 performs convergence determination (details will be described later) when performing local positional alignment. Furthermore, the second registering unit 142 reports the image of the corresponding area obtained by performing the local positional alignment, to the display control unit 143.

The display control unit 143 enlarges and displays an image of a corresponding area 402 reported from the second registering unit 142 on the enlarged display screen on the comparison target CT image. Accordingly, as the image subjected to local positional alignment, the image of the corresponding area 402 including the position of a tumor portion F' corresponding to the tumor portion F, can be displayed.

Note that in FIG. 4, a cross-section 411a schematically indicates the reference cross-section of the image of the predetermined area 401. Similarly, a cross-section 412a schematically indicates the reference cross-section of the image of the corresponding area 402.

Upon accepting an instruction to change the cross-section from the image interpretation doctor with respect to the image of the corresponding area 402 obtained by performing the local positional alignment, the second registering unit 142 performs a cross-section changing process (details will be described later). By performing the cross-section changing process, the second registering unit 142 generates a cross-sectional image of a new cross-section after the change is made, in both the predetermined area 401 and the corresponding area 402.

Accordingly, instead of the image of the predetermined area 401 and the image of the corresponding area 402, the display control unit 143 enlarges and displays the cross-sectional image of the new cross-section in the predetermined area 401 and the corresponding area 402. At this time, the display control unit 143 also displays display information 431 and 432 for indicating the new cross-section (cross-sections 421a and 422a).

In FIG. 4, the cross-section 422a schematically indicates a cross-section used for performing the cross-section changing process on the image of the corresponding area 402. Similarly, the cross-section 421a schematically indicates a cross-section used for performing the cross-section changing process on the image of the predetermined area 401. The cross-sectional position, the cross-sectional direction, and the cross-sectional angle of the cross-section 421a respectively correspond to the cross-sectional position, the cross-sectional direction, and the cross-sectional angle of the cross-section 422a.

Furthermore, when there is an instruction to display a vector (difference vector) indicating the state of convergence with respect to the tumor from the image interpreting doctor, the second registering unit 142 displays the difference vector for the new cross-section in the corresponding area 402.

As described above, according to the cross-sectional image generating apparatus 120, when the position of the tumor portion F is specified by the image interpreting doctor in the comparison source CT image, the image of the predetermined area 401 can be enlarged and displayed. Furthermore, by performing local positional alignment based on the image of the predetermined area 401, it is possible to extract the image of the corresponding area 402 from the comparison target CT image and enlarge and display the extracted image. Furthermore, when an instruction to change the cross-section is accepted from the image interpreting doctor, it is possible to generate a cross-sectional image of a new cross-section by which appropriate image interpretation with respect to the tumor can be promoted, and enlarge and display the generated cross-sectional image on the enlarged display screen. Furthermore, in the cross-sectional image of the new cross-section, a difference vector indicating the state of convergence with respect to on the tumor, can be displayed.

Accordingly, the image interpreting doctor is able to easily recognize the corresponding areas between the CT images included in cross-sectional image groups captured at different time periods, and the image interpreting doctor is able to perform appropriate image interpretation with respect to the tumor.

Next, the image DB 130 that stores the cross-sectional image group processed by the cross-sectional image generating apparatus 120 will be described. FIG. 5 is a diagram illustrating an example of information stored in the image DB. As illustrated in FIG. 5, information stored in the image DB 130 is classified and managed for each patient, and FIG. 5 illustrates an example of information on a patient having a patient ID="xxx".

As illustrated in FIG. 5, the items of the information include "captured date and time", "captured region", "name of series", and "cross-sectional image group". In "captured date and time", information on the date and time when the CT image has been captured, is stored. In "captured region", information on a particular object (region) for which an image has been captured, is stored. In "name of series", a name of a series for identifying a series formed of a plurality of CT images obtained by the capturing, is stored. In "cross-sectional image group", the respective file names of a plurality of CT images (cross-sectional image group with respect to the reference cross-section) obtained by the capturing, are stored.

The example of FIG. 5 indicates that a series, which has a series name="series A" including the CT images of ImageA001 to ImageA030 obtained by capturing the captured region="lung" on the captured date and time="2014.2.5", is stored in the image DB 130. Furthermore, the example of FIG. 5 indicates that a series, which has a series name="series B" including CT images of ImageB001 to ImageB030 obtained by capturing the captured region="lung" on the captured date and time="2014.8.3", is stored in the image DB 130.

Note that a part surrounded by dotted lines in FIG. 5 indicates that the CT image of "ImageA015" has been selected by the image interpreting doctor as the comparison source CT image. Furthermore, another part surrounded by dotted lines in FIG. 5 indicates that the CT image of "ImageB018" has been selected by the image interpreting doctor as the comparison target CT image.

Next, each unit of the image interpretation supporting unit 140 will be described. Note that in the following, descriptions of the first registering unit 141 and the display control unit 143 will be omitted, and the second registering unit 142 will be mainly described.

As described above, at the time when global positional alignment is completed, the overall positional variation is corrected between the comparison source CT image and the comparison target CT image; however, local positional variations still remain. Therefore, when enlarging and displaying the image of the corresponding area 402 corresponding to the predetermined area 401 including the position of the tumor portion F specified by the image interpreting doctor, the second registering unit 142 first obtains the local positional variation of the comparison target CT image with respect to the comparison source CT image. Then, in accordance with the obtained variation, the second registering unit 142 performs local positional alignment by performing a conversion process by parallel movement on the comparison target CT image. Accordingly, the second registering unit 142 can extract the image of the corresponding area 402.

Here, in the case of captured region="lung", there are two factors as the main factors causing local positional variations (a factor based on respiration/heartbeat and a factor based on change in the tumor (change with time)). FIG. 6 is a diagram illustrating factors of local positional variations in the comparison target CT image with respect to the comparison source CT image.

When a local positional variation occurs, as illustrated in FIG. 6, for example, an image 610, is extracted from an area in the comparison target CT image having the same coordinates as the predetermined area 401 in the comparison source CT image.

In FIG. 6, by comparing an image 600 of the predetermined area 401 in the comparison source CT image with the image 610 of the area in the comparison target CT image having the same coordinates as the predetermined area 401, it can be seen that both the positions of blood vessels and the position of the tumor are largely deviated between these two images. Note that in FIG. 6, thick lines indicate blood vessels 601 to 603 and 611 to 613, and shaded areas indicate tumor portions F and F'.

Here, the positional variation based on the respiration/heartbeat means the positional variation caused by the movement of the diaphragm at the time of respiration, for example. Since the position of the diaphragm varies between a case where the patient breathes out and a case where the patient breathes in, the position of each part in the lung varies accordingly. As a result, between the comparison source CT image and the comparison target CT image, local positional variations based on the respiration/heartbeat are included, except for a case where the states of breathing by the patient are perfectly matching at the time points when the images have been captured.

Note that the positional variation based on respiration/heartbeat is, for example, a non-rigid body deformation with respect to the whole body; however, since the predetermined area 401 is a part of the lung, the entire predetermined area 401 is moved in a parallel manner in a predetermined direction. Therefore, in the predetermined area 401, the positional variation based on respiration/heartbeat can be regarded as a rigid body motion.

On the other hand, the positional variation based on the change in the tumor means a positional variation that is caused as a malignant tumor such as an adenocarcinoma, etc., proliferates while destroying the alveoli, and the alveolar volume decreases by the amount of air that the alveolus has retained, etc.

The second registering unit 142 extracts the positional variation based on the respiration/heartbeat by subtracting the positional variation based on a change in the tumor (change with time), among the positional variations based on the above two factors. Then, the second registering unit 142 performs local positional alignment based on the positional variation based on the respiration/heartbeat.

Figure 7:
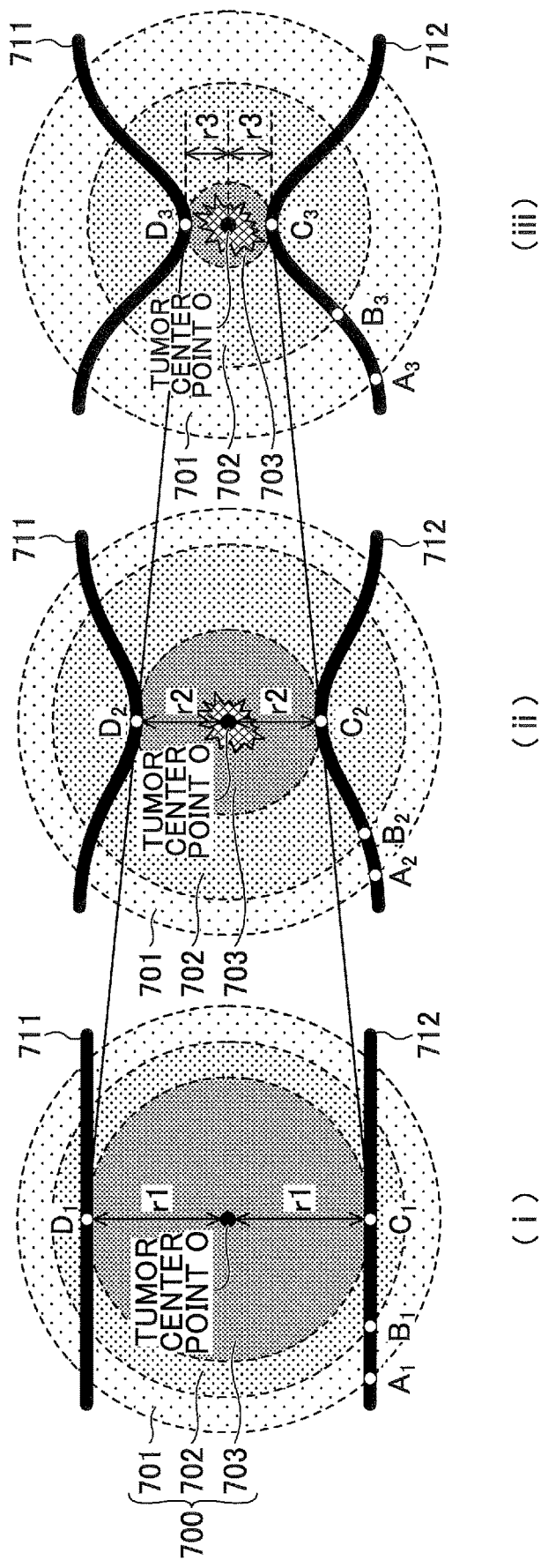
FIG. 7 is a diagram for describing the positional variation based on the change in the tumor in further detail.

Here, the positional variation based on the change in the tumor (change with time) will be described in more detail with reference to FIG. 7. FIG. 7 is a diagram for describing the positional variation based on the change in the tumor in further detail.

FIG. 7 ($i$) illustrates the state of surrounding tissues immediately after a malignant tumor such as an adenocarcinoma develops at the position indicated at a tumor center point O. As illustrated in FIG. 7 ($i$), in a state immediately after a malignant tumor has developed, the distance from the tumor center point O to a point $D_1$ of a bronchus 711, and the distance from the tumor center point O to a point $C_1$ of a blood vessel 712, are each r1.

FIG. 7 ($ii$) illustrates that the surrounding tissue including the bronchus 711 and the blood vessel 712 has moved toward the tumor center point O, because the malignant tumor has proliferated while destroying the alveoli around the tumor. As illustrated in FIG. 7 ($ii$), as the surrounding tissue has moved toward the tumor center point O, the distance from the tumor center point O to a point $D_2$ of the bronchus 711 and the distance from the tumor center point O to a point $C_2$ of the blood vessel 712, are each r2 (<r1).

FIG. 7 ($iii$) illustrates that the surrounding tissue including the bronchus 711 and the blood vessel 712 has moved further toward the tumor center point O, because the malignant tumor has further proliferated while further destroying the alveoli around the tumor. As illustrated in FIG. 7 ($iii$), as the surrounding tissue has moved toward the tumor center point O, the distance from the tumor center point O to a point $D_3$ of the bronchus 711 and the distance from the tumor center point O to a point $C_3$ of the blood vessel 712 are each r3 (<r2).

In this way, the positional variation based on a change in the tumor has a characteristic that the surrounding tissue moves toward the tumor center point O, and this positional variation can be regarded as a non-rigid body deformation.

As illustrated in FIG. 7, the surrounding tissue of the tumor can be roughly divided into the tissue in a tumor area 703, the tissue in a convergence area 702, and the tissue in a normal area 701. In the tumor area 703, a portion of the tissue existing in FIG. 7 ($i$) disappears because this tissue is destroyed by a newly appearing malignant tumor, and this tissue does not exist in FIG. 7 ($iii$). On the other hand, in the convergence area 702, although the tissue that has existed in FIG. 7 ($i$) also exists in FIG. 7 ($iii$), the position of the corresponding tissue varies (B1→B2→B3). Furthermore, in the normal area 701, the tissue existing in FIG. 7 ($i$) also exists in FIG. 7 (iii), and the position of the corresponding tissue has not appreciably moved (A1→A2→A3).

As apparent from the description of FIGS. 6 and 7, as factors of local positional variations between the comparison source CT image and the comparison target CT image, there is a factor "based on respiration/heartbeat" that is regarded as a rigid body motion, and a factor "based on a change in the tumor" that is regarded as non-rigid body deformation. Furthermore, in the case of the factor "based on a change in the tumor", there is a characteristic of moving toward the tumor center point O, and depending on the degree of the movement, the tissue surrounding the tumor can be roughly divided into the normal area 701, the convergence area 702, and the tumor area 703.

Figure 8:
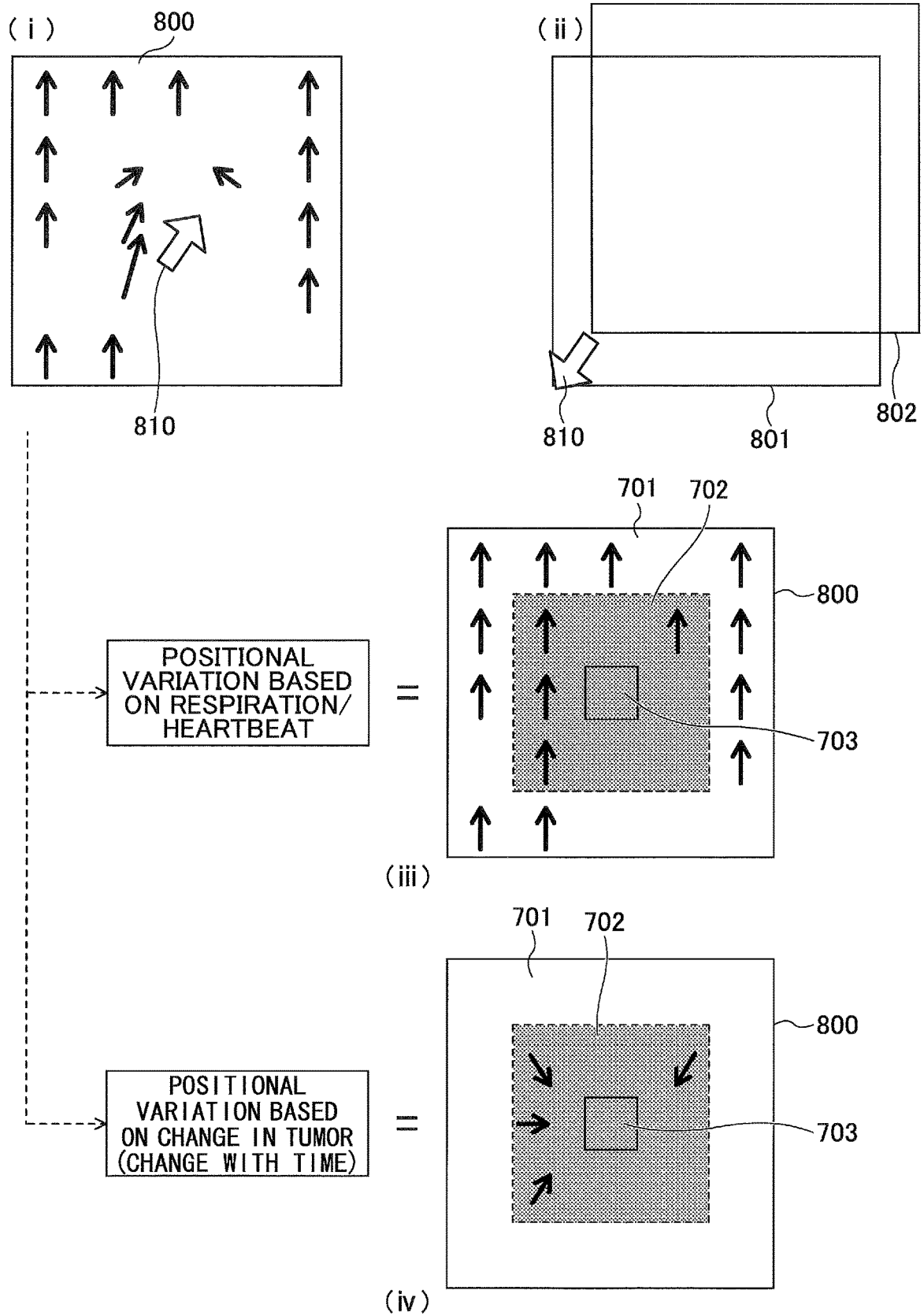
FIG. 8 is a diagram for describing a process of calculating a representative vector and a process of calculating a corresponding area.
Figure 9:
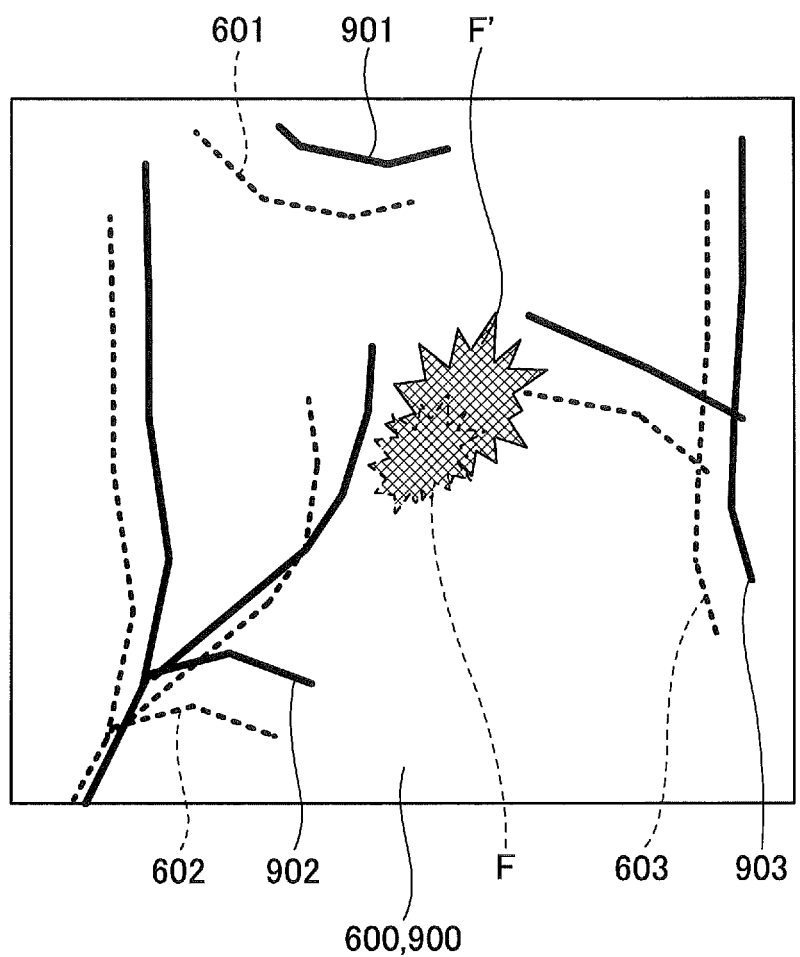
FIG. 9 is a diagram illustrating an image subjected to local positional alignment by using a representative vector including the influence of non-rigid body deformation.

Next, with reference to FIGS. 8 and 9, a description is given of a problem that arises when the second registering unit 142 performs positional alignment with respect to an area where a rigid body motion and a non-rigid body deformation are both present as illustrated in FIG. 6, in the comparison target CT image.

As described above, when performing local positional alignment in the comparison target CT image, the second registering unit 142 performs the conversion process by a parallel movement. That is, a conversion process assuming a rigid body is performed, instead of a conversion process assuming a non-rigid body.

Here, in performing the conversion process by parallel movement, the second registering unit 142 calculates a representative vector indicating the position in the comparison target CT image to which the predetermined area 401 has moved (the positional relationship between the predetermined area 401 and the corresponding area 402).

FIG. 8 is a diagram for describing a process of calculating a representative vector and a process of calculating a corresponding area. FIG. 8 (i) illustrates corresponding vectors (black arrows) indicating the difference between the positions of feature points included in the predetermined area 401 of the comparison source CT image and the positions of the corresponding feature points in the comparison target CT image. Note that an area 800 is an area including the feature points in the comparison target CT image corresponding to the feature points included in the predetermined area 401 of the comparison source CT image, and the area 800 is used for calculating the representative vector. Hereinafter, this area in the comparison target CT image is referred to as a representative vector calculation target area 800.

That is, in the second registering unit 142, the predetermined area 401 in the comparison source CT image and the representative vector calculation target area 800 in the comparison target CT image, are data indicating the internal structure of the tumor and the tissue surrounding the tumor included in the region (lung) of the captured images.

Here, it is assumed that the second registering unit 142 calculates a representative vector 810 by using all corresponding vectors included in the representative vector calculation target area 800. In this case, the image subjected to local positional alignment can be extracted by executing the process illustrated in FIG. 8 (ii).

FIG. 8 (ii) illustrates how an image subjected to local positional alignment is being extracted from the comparison target CT image, by performing a conversion process by parallel movement with the use of the representative vector 810. As illustrated in FIG. 8 (ii), the second registering unit 142 moves, by parallel movement, an area 801 in the comparison-target CT image having the same coordinates as the predetermined area 401 in the comparison source CT image based on the representative vector 810, thereby obtaining an area 802. Then, by extracting the image of the area 802 from the comparison target CT image, the image subjected to local positional alignment is extracted.

However, the image extracted in this manner is obtained as follows. Specifically, in the area where a rigid body motion and a non-rigid body deformation area are both present, the representative vector is obtained by assuming that only the rigid body motion is occurring, and the image is moved in parallel so as to cancel out the rigid body motion. That is, the image is moved in parallel so as to cancel out also the influence of the non-rigid body deformation.

Further details will be described with reference to FIGS. 8 (iii) and 8 (iv). FIG. 8 (iii) illustrates the corresponding vectors indicating the positional variation based on respiration/heartbeat (based on the rigid body motion), among the corresponding vectors connecting positions of feature points included in the predetermined area 401 in the comparison source CT image with positions of the corresponding feature points in the comparison target CT image. As illustrated in FIG. 8 (iii), the corresponding vectors indicating the rigid body motion all face the same direction, and all have the same length. Note that the corresponding vectors indicating the rigid body motion exist in the normal area 701 and the convergence area 702. However, in the tumor area 703, there are no feature points of the comparison target CT image corresponding to the feature points of the comparison source CT image, and therefore no corresponding vectors are present.

On the other hand, FIG. 8 (iv) illustrates the corresponding vectors indicating the positional variation based on a change in the tumor (based on the non-rigid body deformation), among the corresponding vectors connecting positions of feature points included in the predetermined area 401 of the comparison source CT image with positions of the corresponding feature points in the comparison target CT image. As illustrated in FIG. 8 (iv), the corresponding vectors of the non-rigid body deformation exist only in the convergence area 702 (excluding the tumor area 703), and these corresponding vectors face the center direction.

As described above, there is a difference in the length and the direction of vectors, and there is also a difference in the positions of the vectors, between the corresponding vectors indicating the rigid body motion and the corresponding vectors indicating the non-rigid body deformation.

Note that the corresponding vectors illustrated in FIG. 8 (i) are obtained by adding the corresponding vectors illustrated in FIG. 8 (iii) and the corresponding vectors illustrated in FIG. 8 (iv).

Said differently, the corresponding vectors indicating the rigid body motion and the corresponding vectors indicating the non-rigid body deformation are both present, among the corresponding vectors existing at the position corresponding to the convergence area 702, among the corresponding vectors illustrated in FIG. 8 (i). Therefore, when the representative vector 810 is calculated by including the corresponding vectors existing at the position corresponding to the convergence area 702, the representative vector 810 includes the influence of the non-rigid body deformation. Thus, even by performing local positional alignment by using the representative vector 810, it is not possible to perform positional alignment with high accuracy.

A description will be given by using a specific image. FIG. 9 is a diagram illustrating an image subjected to local positional alignment by using a representative vector including the influence of non-rigid body deformation. Note that in the example of FIG. 9, an image 900 subjected to local positional alignment (the image of the area 802 in the comparison target CT image), and the image 600 of the predetermined area 401 in the comparison source CT image, are superimposed.

As illustrated in FIG. 9, the positions of blood vessels 901 to 903 and the tumor portion F' included in the image 900 are deviated with respect to the positions of the blood vessels 601 to 603 and the tumor portion F included in the image 600, even though the local positional alignment has been performed.

In consideration of the above problems that arise in calculating the representative vector in an area where the rigid body motion and the non-rigid body deformation are both present, the second registering unit 142 according to the first embodiment obtains a representative vector upon eliminating the influence of the non-rigid body deformation, and performs local positional alignment.

Furthermore, the second registering unit 142 according to the first embodiment performs a cross-section changing process of changing the image of the corresponding area 402 obtained by performing local positional alignment, to a cross-sectional image of a cross-section where the influence of non-rigid deformation appears more significantly.

Thus, according to the first embodiment, it is possible to display a cross-sectional image of a cross-section where the influence of non-rigid deformation (that is, the positional variation based on the change in the tumor (change with time)) appears more significantly, with respect to the corresponding area obtained by performing local positional alignment so as to cancel out the positional variation based on respiration/heartbeat.

Note that in the second registering unit 142, calculating the positional variation based on the change in the tumor (change with time) is equivalent to detecting the structural change in the internal structure of the tumor and the tissue surrounding the tumor. Said differently, calculating the positional variation based on the change in the tumor (change with time) is equivalent to detecting a structural change from the internal structure expressed in the image of the predetermined area 401, in the internal structure expressed in the image of the representative vector calculation target area 800.

In the following, the functional configuration of the second registering unit 142 according to the first embodiment will be described with reference to FIG. 10, and with reference to FIG. 11 through FIG. 16, details of the contents of processes by each unit forming the second registering unit 142 will be described. Furthermore, with reference to the flowcharts of FIGS. 17 to 21, the flows of processes executed by the second registering unit 142 will be described.

Figure 10:
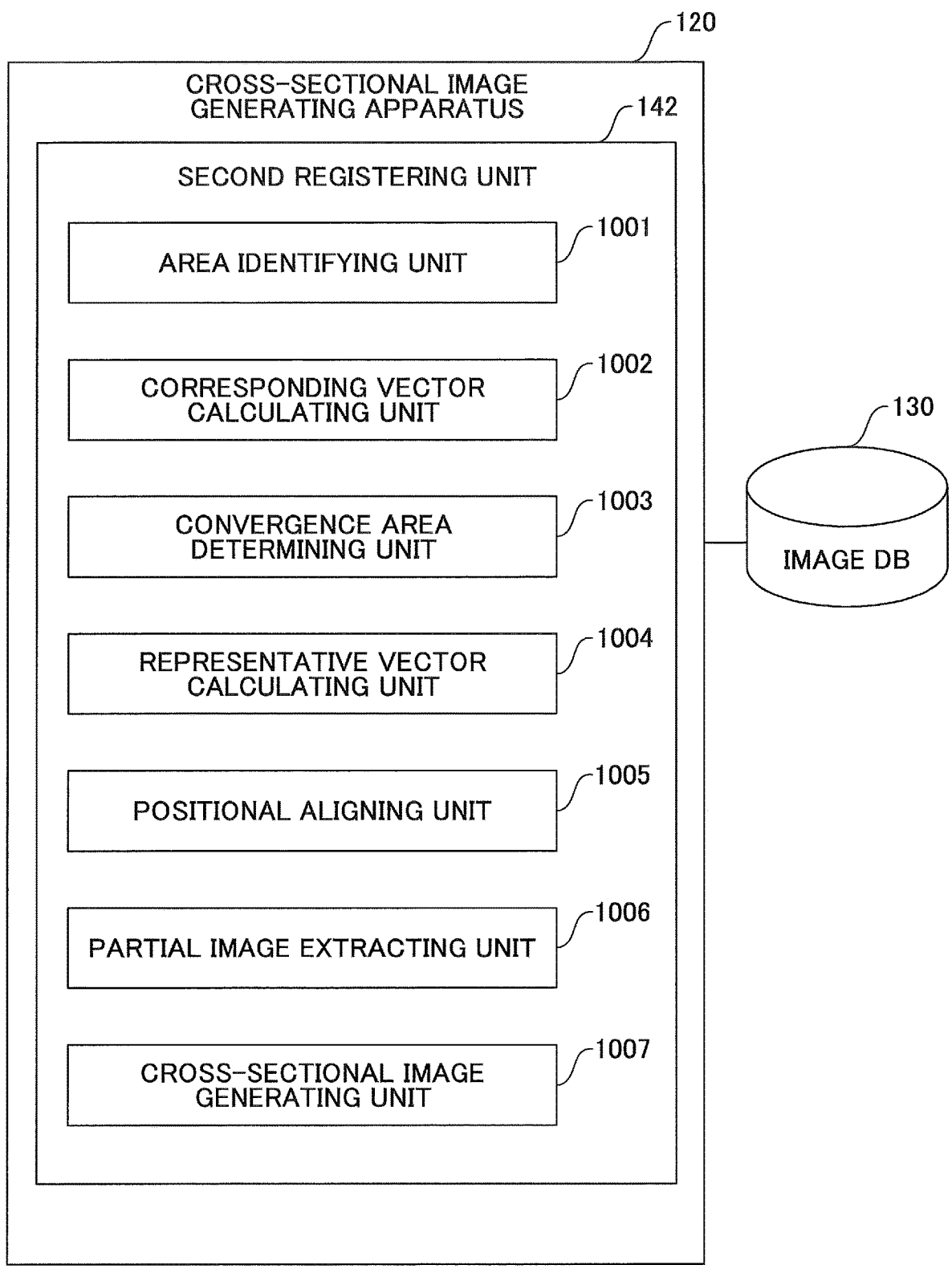
FIG. 10 is a diagram illustrating the functional configuration of a second registering unit.

FIG. 10 is a diagram illustrating the functional configuration of the second registering unit 142. As illustrated in FIG. 10, the second registering unit 142 includes an area identifying unit 1001, a corresponding vector calculating unit 1002, a convergence area determining unit 1003, a representative vector calculating unit 1004, and a positional aligning unit 1005. Furthermore, the second registering unit 142 includes a partial image extracting unit 1006 and a cross-sectional image generating unit 1007.

The area identifying unit 1001 identifies the predetermined area 401 including a position specified by the image interpreting doctor. Specifically, the area identifying unit 1001 acquires the coordinates in the comparison source CT image that identify the position of the predetermined area 401.

The corresponding vector calculating unit 1002 extracts feature points from the predetermined area 401 of the comparison source CT image identified by the area identifying unit 1001. Furthermore, the corresponding vector calculating unit 1002 searches for each feature point in the comparison target CT image corresponding to each of the extracted feature points. Furthermore, based on the difference between the position of each feature point extracted from the comparison source CT image and the position of the corresponding feature point in the comparison target CT image, the corresponding vector calculating unit 1002 calculates a corresponding vector.

Based on the corresponding vectors calculated by the corresponding vector calculating unit 1002, the convergence area determining unit 1003 determines whether the convergence area 702 is included in the representative vector calculation target area 800. Furthermore, when the convergence area determining unit 1003 determines that the convergence area 702 is included, the convergence area determining unit 1003 calculates the boundary position between the normal area 701 and the convergence area 702. Furthermore, the convergence area determining unit 1003 reports, to the representative vector calculating unit 1004, the determination result on whether the convergence area 702 is included and the calculation result of the boundary position between the normal area 701 and the convergence area 702.

The representative vector calculating unit 1004 calculates a representative vector in the representative vector calculation target area 800 based on the corresponding vectors calculated by the corresponding vector calculating unit 1002. When the representative vector calculating unit 1004 determines that the convergence area 702 is not included in the representative vector calculation target area 800, the representative vector calculating unit 1004 calculates all of the corresponding vectors (excluding the tumor area) in the representative vector calculation target area 800 to calculate a representative vector. Conversely, when the representative vector calculating unit 1004 determines that the convergence area 702 is included in the representative vector calculation target area 800, the representative vector calculating unit 1004 calculates the representative vector by using the corresponding vectors excluding corresponding vectors included in the convergence area (and the tumor area), among the corresponding vectors in the representative vector calculation target area 800.

Note that in the first embodiment, the representative vector calculating unit 1004 performs an averaging process to calculate the representative vector by using the corresponding vectors.

The positional aligning unit 1005 extracts the image of the corresponding area 402 corresponding to the predetermined area 401, from the comparison target CT image, based on the representative vector calculated by the representative vector calculating unit 1004. Specifically, the positional aligning unit 1005 calculates the coordinates after the movement of moving the coordinates identifying the position of the predetermined area 401 in the comparison target CT image by using the representative vector. Furthermore, the positional aligning unit 1005 acquires the image subjected to local positional alignment by extracting, from the comparison target CT image, an image of the area (corresponding area 402) identified by the calculated coordinates after movement.

Note that in the first embodiment, the units from the area identifying unit 1001 to the positional aligning unit 1005 do not only execute processes on the comparison source CT image and the comparison target CT image, but also execute the same processes on the CT images of the preceding and subsequent layers. The CT images of layers before or after the comparison source CT image means, for example, CT images having file names="ImageA010" to "ImageA014" when the comparison source CT image has the file name="ImageA015". Alternatively, CT images of layers before or after the comparison source CT image mean, for example, CT images having file names="ImageA016" to "ImageA020". Furthermore, the CT images of the layers before or after the comparison target CT image are, for example, CT images having the file names="ImageB014" to "ImageB017" when the comparison target CT image is a CT image having a file name="ImageB018", etc. Alternatively, the CT images of the layers before or after the comparison target CT image are, for example, CT images having file names="ImageB019" to "ImageB022".

Therefore, based on the comparison source CT image and the CT images of the layers before and after the comparison source CT image, the area identifying unit 1001 functions as a generating unit that generates an image of the predetermined area 401, which is data indicating the internal structure of the tumor and surrounding tissues.

Furthermore, based on the comparison target CT image and the CT images of the layers before and after the comparison target CT image, the corresponding vector calculating unit 1002 functions as a generating unit that generates the image of the representative vector calculation target area 800, which is data indicating the internal structure of the tumor and surrounding tissues.

Furthermore, based on the image of the predetermined area 401 generated by the area identifying unit 1001 and the image of the representative vector calculation target area 800 generated by the corresponding vector calculating unit 1002, the convergence area determining unit 1003 functions as a detecting unit that detects the structural change.

The partial image extracting unit 1006 identifies a cross-section different from the reference cross-section with respect to the corresponding area 402, when an instruction to change the cross-section is given from the image interpreting doctor. Furthermore, the partial image extracting unit 1006 extracts partial images for generating a cross-sectional image with respect to the identified cross-section, from the comparison target CT image and the CT images of layers before and after the comparison target CT image. Similarly, the partial image extracting unit 1006 identifies a cross-section different from the reference cross-section with respect to the predetermined area 401. Furthermore, the partial image extracting unit 1006 extracts partial images for generating a cross-sectional image of the identified cross-section, from the comparison source CT image and the CT images of the layers before and after the comparison source CT image.

The cross-sectional image generating unit 1007 generates a cross-sectional image of a cross-section different from the reference cross-section, and reports the cross-sectional image to the display control unit 143. Specifically, the cross-sectional image generating unit 1007 generates a cross-sectional image by using the partial images extracted from the comparison source CT image and the CT images of the layers before and after the comparison source CT image by the partial image extracting unit 1006, and reports the generated cross-sectional image to the display control unit 143. Furthermore, the cross-sectional image generating unit 1007 generates a cross-sectional image by using the partial images extracted from the comparison target CT image and the CT images of the layers before and after the comparison target CT image by the partial image extracting unit 1006, and reports the generated cross-sectional image to the display control unit 143. Note that when reporting the generated cross-sectional image to the display control unit 143, the cross-sectional image generating unit 1007 also reports the display information 431 and 432 for indicating the cross-sections used for generation.

Furthermore, when there is an instruction to display a difference vector from the image interpreting doctor, the cross-sectional image generating unit 1007 superimposes, on the generated cross-sectional image, the difference vectors included in the partial images extracted from the comparison target CT image and the CT images of the layers before and after the comparison target CT image. Furthermore, the cross-sectional image generating unit 1007 reports the cross-sectional image on which the difference vectors are superimposed, to the display control unit 143.

That is, the cross-sectional image generating unit 1007 functions as a generating unit that generates a cross-sectional image of a new cross-section that is different from the reference cross-section. Furthermore, the display control unit 143 functions as a display unit that displays the generated cross-sectional image together with difference vectors (information indicating a structural change).

Next, a description will be given of specific examples of the contents of processes respectively executed by the convergence area determining unit 1003, the representative vector calculating unit 1004, the positional aligning unit 1005, the partial image extracting unit 1006, and the cross-sectional image generating unit 1007, among the units included in the second registering unit 142 illustrated in FIG. 10.

First, a specific example of the contents of processes executed by the convergence area determining unit 1003 will be described. FIG. 11 is a diagram illustrating the contents of processes executed by the convergence area determining unit 1003.

The example of FIG. 11 illustrates that the area from the center to the periphery of the representative vector calculation target area 800 is divided into segments having a predetermined pitch width in a rectangular frame shape, and it is determined whether the convergence area 702 is included in the representative vector calculation target area 800 based on the corresponding vectors in the respective segments.

Note that the distance from the center to the periphery of the representative vector calculation target area 800 is R and the pitch width is ΔR. Furthermore, although the case of dividing the area into a rectangular frame shape is described here, instead of dividing the area into a rectangular frame shape, the area may be divided into a circular ring shape.

The convergence area determining unit 1003 extracts corresponding vectors included in a segment group 1101 within the range of R to (R-ΔR) (hatched area in the representative vector calculation target area 800 illustrated at the left end of FIG. 11). Furthermore, the convergence area determining unit 1003 extracts corresponding vectors included in a segment group 1102 within the range of (R−ΔR) to (R−ΔR×2) (the hatched area in the representative vector calculation target area 800 illustrated in the center of FIG. 11).

Then, the convergence area determining unit 1003 calculates the difference between adjacent corresponding vectors, between the corresponding vectors in the segment group 1101 and the corresponding vectors in the segment group 1102, from among the extracted corresponding vectors, and obtains difference vectors. The difference vectors thus obtained may be referred to as indicating the differences in the positional variations of the feature points between the comparison source CT image and the comparison target CT image. Each of the vectors in the representative vector calculation target area 800 illustrated at the right end of FIG. 11 illustrates an example of a difference vector calculated based on a corresponding vector in the segment group 1101 and a corresponding vector in the segment group 1102.

When the difference vector thus obtained is larger than a predetermined threshold value, the convergence area determining unit 1003 determines the direction of the difference vector. Furthermore, when it can be considered that the direction of the difference vector is directed toward the center of the representative vector calculation target area 800, the convergence area determining unit 1003 determines that the convergence area is included. Furthermore, the convergence area determining unit 1003 determines, as a boundary position between the normal area 701 and the convergence area 702, a boundary position between two segment groups including the corresponding vectors that have been used to calculate the difference vector used for determining that the convergence area is included.

Note that as is clear from the description of FIG. 11, the convergence area determining unit 1003 first obtains difference vectors by using the corresponding vectors extracted from the outermost segment group 1101 of the representative vector calculation target area 800. This is because it is possible to estimate that the corresponding vectors are corresponding vectors that are not influenced by a positional variation based on a change in the tumor, and are corresponding vectors according to a positional variation based on respiration/heartbeat.

Furthermore, the convergence area determining unit 1003 calculates the difference between vectors adjacent to each other. This is because there is no large difference between adjacent vectors in the positional variation based on respiration/heartbeat, and by calculating this difference, the influence of the positional variation based on respiration/heartbeat can be subtracted. That is, it can be said that a difference vector (however, a difference vector having a size that is greater than or equal to a predetermined threshold), obtained by calculating the difference between adjacent corresponding vectors, is a corresponding vector indicating the positional variation based on a change in the tumor (that is, information indicating a structural change).

Note that the reason why the convergence area determining unit 1003 determines the direction of the difference vector, is that the corresponding vectors in the convergence area have a characteristic of being directed in the direction of the tumor center point O. Therefore, this determination is effective for identifying that the positional variation is based on a change in the tumor.

Next, a specific example of contents of the process by the representative vector calculating unit 1004 will be described. FIGS. 12A and 12B are diagrams illustrating a method of calculating a representative vector in a case where it is determined that there is a convergence area.

When the convergence area 702 is included in the representative vector calculation target area 800, the representative vector calculating unit 1004 obtains a representative vector by excluding the corresponding vector in the convergence area 702, from the calculated corresponding vectors in the representative vector calculation target area 800. In the example of FIG. 12A, 15 corresponding vectors (black arrows) are calculated in the representative vector calculation target area 800, among which four corresponding vectors existing in the convergence area 702 are excluded, so that the remaining 11 corresponding vectors are used for calculating a representative vector.

A representative vector 1200 indicates a representative vector calculated by using eleven corresponding vectors. In this way, by excluding the four corresponding vectors existing in the convergence area 702, it is possible to eliminate the influence of the non-rigid body deformation (that is, the positional variation based on the change in the tumor (change with time)) in calculating the representative vector.

FIG. 12B illustrates a state of extracting an image subjected to local positional alignment, from the comparison target CT image, by performing a conversion processing by parallel movement by using the representative vector 1200. As illustrated in FIG. 12B, the second registering unit 142 moves, in parallel, the area 801 in the comparison target CT image corresponding to the predetermined area 401 in the comparison source CT image, according to the representative vector 1200, thus obtaining the corresponding area 402. Furthermore, by extracting the image of the corresponding area 402 from the comparison target CT image, the second registering unit 142 can extract the image subjected to local positional alignment.

Conversely, FIGS. 13A and 13B are diagrams illustrating a method of calculating the representative vector in a case where it is determined that there is no convergence area. When the convergence area 702 is not included in the representative vector calculation target area 800, the representative vector calculating unit 1004 calculates a representative vector by using the calculated corresponding vectors in the representative vector calculation target area 800. However, it is assumed that the corresponding vectors included in the tumor area 703 are excluded. Note that in the tumor area 703, there is no corresponding point of a feature point, and therefore there is no corresponding vector, so that regardless of whether the corresponding vectors existing in the tumor area 703 are excluded, the calculated representative vector will be the same.

In the example of FIG. 13A, 15 corresponding vectors (black arrows) are calculated in the representative vector calculation target area 800, and the representative vector calculating unit 1004 calculates a representative vector by using the 15 corresponding vectors. A representative vector 1300 indicates the representative vector calculated by using the 15 corresponding vectors. In this way, when the convergence area 702 is not included in the representative vector calculation target area 800, there will be no influence of a non-rigid body deformation, and it therefore becomes possible to calculate the representative vector by using all corresponding vectors.

FIG. 13B illustrates a state of extracting an image subjected to local positional alignment, from a comparison target CT image, by performing a conversion process by parallel movement by using the representative vector 1300. As illustrated in FIG. 13B, the second registering unit 142 moves in parallel, the area 801 in the comparison target CT image corresponding to the predetermined area 401 in the comparison source CT image according to the representative vector 1300, thus obtaining the corresponding area 402. Furthermore, by extracting the image of the corresponding area 402 from the comparison target CT image, the second registering unit 142 can extract the image subjected to local positional alignment.

Figure 14:
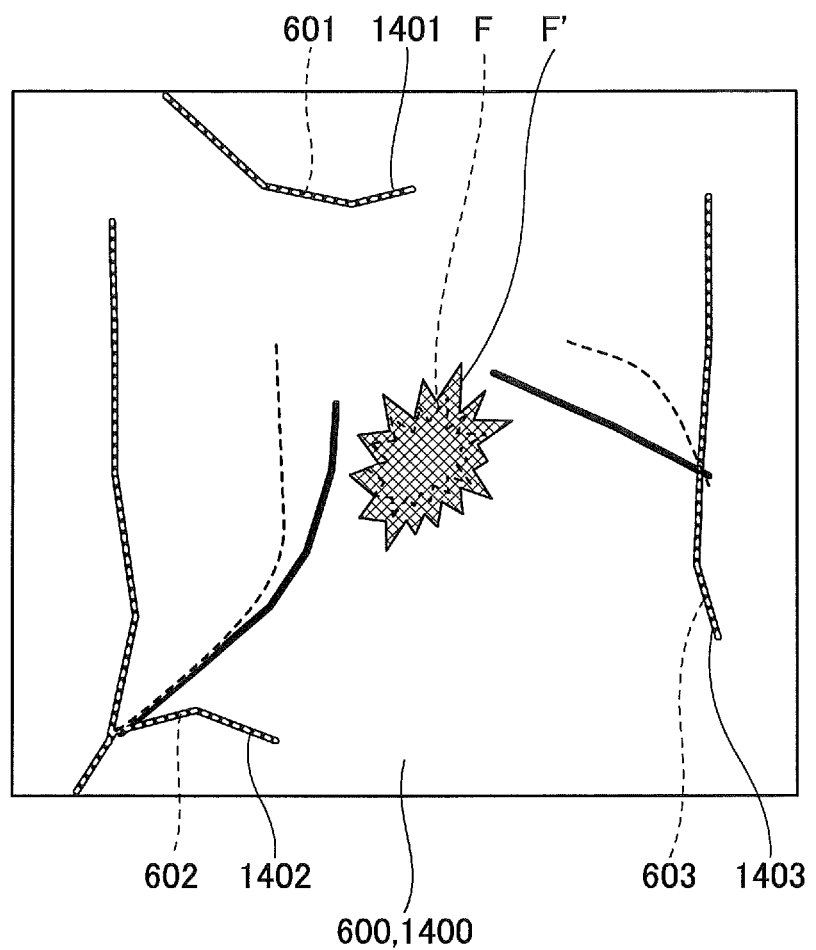
FIG. 14 is a diagram illustrating an image obtained by performing local positional alignment by using a representative vector excluding the influence of non-rigid body deformation.

Here, an image of the corresponding area 402 obtained by performing local positional alignment by the positional aligning unit 1005 by using the representative vector 1200 excluding the influence of non-rigid body deformation will be described. FIG. 14 is a diagram illustrating an image obtained by performing local positional alignment by using a representative vector excluding the influence of non-rigid body deformation.

Note that in the example of FIG. 14, an image 1400 of the corresponding area 402 in the comparison target CT image, and the image 600 of the predetermined area 401 in the comparison source CT image, are superimposed.

As illustrated in FIG. 14, the positions of blood vessels 1401 to 1403 and the tumor portion F' included in the image 1400, are substantially the same as the positions of the blood vessels 601 to 603 and the tumor portion F included in the image 600. That is, in the case of the image 1400, the positional variation based on respiration/heartbeat is canceled out. On the other hand, among the blood vessels 1402 and 1403, blood vessels located around the tumor portion F' are deviated in position with respect to the blood vessels located around the tumor portion F among the blood vessels 601 to 603 included in the image 600. That is, in the case of the image 1400, the influence of the positional variation based on the change in the tumor remains.

Next, a specific example of contents of processes by the partial image extracting unit 1006 will be described. FIGS. 15A through 15C are diagrams illustrating contents of processes by the partial image extracting unit 1006. FIG. 15A illustrates display information 432 for indicating a cross-section. Note that the x axis illustrated in FIG. 15A indicates the lateral direction of the patient, and the y axis illustrated in FIG. 15A indicates the anteroposterior direction of the patient. Furthermore, the z axis illustrated in FIG. 15A indicates the vertical direction of the patient. On the other hand, FIGS. 15B and 15C illustrate corresponding areas and partial images of the respective layers before and after the comparison target CT image.

As illustrated in FIGS. 15A through 15C, the partial image extracting unit 1006 acquires the image of the corresponding area 402 included in the comparison target CT image (file name="ImageB018") from the positional aligning unit 1005. Furthermore, the partial image extracting unit 1006 extracts a partial image 1514 including a tumor, from the image of the corresponding area 402. Note that when a difference vector is included in the range identified by the partial image 1514, the difference vector is also extracted.

Similarly, the partial image extracting unit 1006 extracts, from the image of a corresponding area 1503 included in a CT image (file name="ImageB017") of the immediately preceding layer of the comparison target CT image, partial images 1513 corresponding to the cross-section 422a.

Similarly, the partial image extracting unit 1006 extracts, from the images of corresponding areas 1502 and 1501 included in the CT images (file names="ImageB016" and "Image B015") of the layers before the comparison target CT image, partial images 1512 and 1511 corresponding to the cross-section 422a.

Furthermore, the partial image extracting unit 1006 extracts, from the image of a corresponding area 1505 included in the CT image (file name="Image B019") of a layer that is one layer after the comparison target CT image, partial images 1515 corresponding to the cross-section 422a.

Similarly, the partial image extracting unit 1006 extracts, from the images of corresponding areas 1506 and 1507 included in the CT images (file names="Image B020" and "Image B021") of the layers after the comparison target CT image, partial images 1516 and 1517 corresponding to the cross-section 422a.

Figure 16:
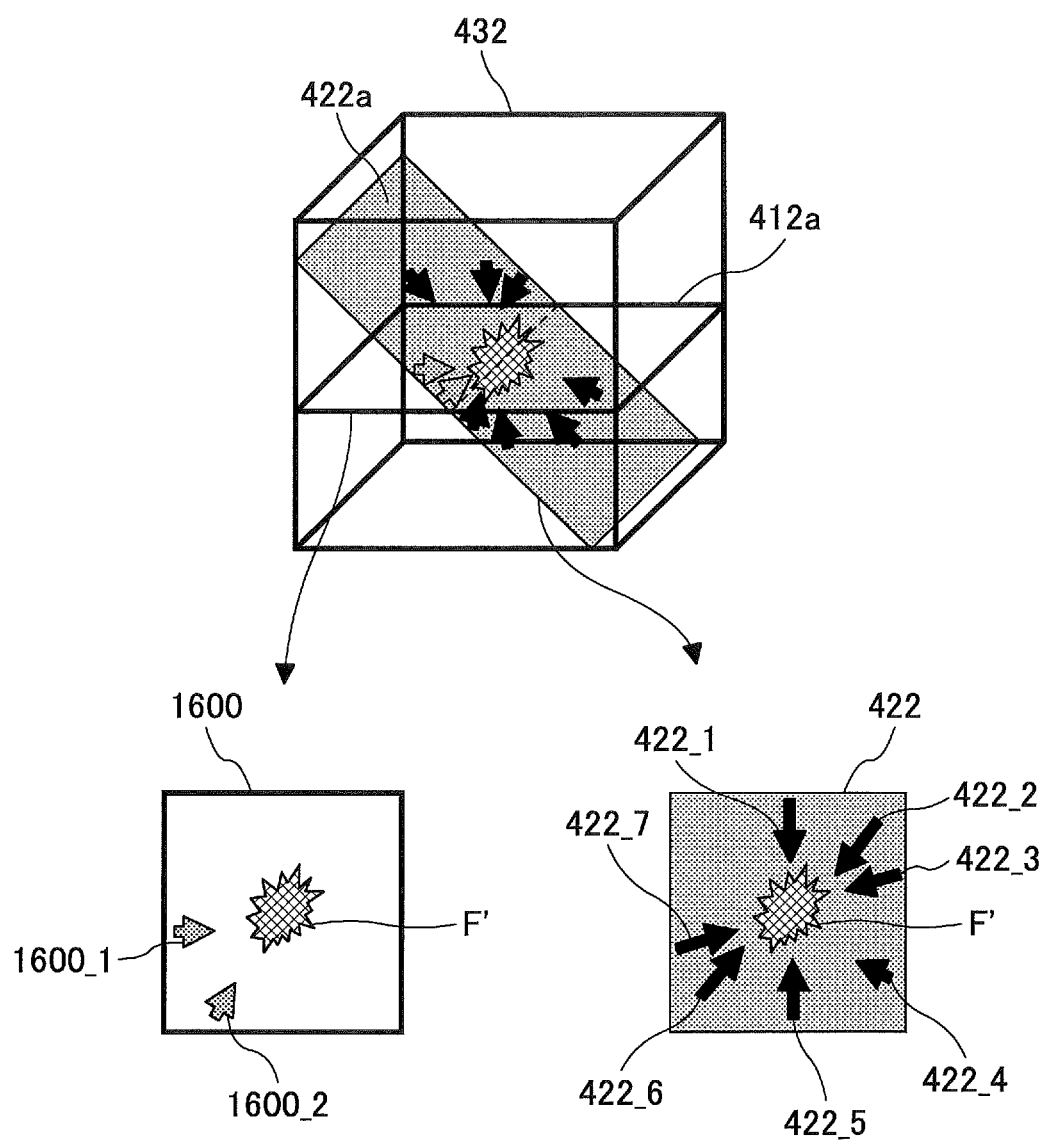
FIG. 16 is a diagram illustrating contents of processes by a cross-sectional image generating unit according to the first embodiment.

Next, a specific example of contents of processes by the cross-sectional image generating unit 1007 will be described. FIG. 16 is a diagram illustrating contents of processes by the cross-sectional image generating unit 1007.

The cross-sectional image generating unit 1007 generates a cross-sectional image (cross-sectional image of the cross-section 422a) based on the partial images 1511 to 1517 (see FIG. 15B) extracted by the partial image extracting unit 1006. A cross-sectional image 422 of the cross-section 422a is a cross-sectional image in a case where the surrounding tissue of the patient's tumor is viewed from a direction substantially orthogonal to the cross-section 422a.

In the example of FIG. 16, as a matter of comparison, a cross-sectional image 1600 (=the image 1400 of the corresponding area 402 in the comparison target CT image) of the cross-section 412a that is the reference cross-section, is also illustrated. As illustrated in FIG. 16, the number and size of the difference vectors included in the cross-sectional image 1600 of the cross-section 412a are not equal to the number and size of the difference vectors included in the cross-sectional image 422 of the cross-section 422a.

This is because the convergence per se is considered to be occurring uniformly; however, tissues such as blood vessels, for which a change with time (movement) accompanying the convergence is observed, are not necessarily uniformly distributed in the lung. Therefore, when a tissue such as a blood vessel for which a difference vector is observed, is close to the tumor, the tissue receives a strong converging force and the difference vector will indicate a large movement; and conversely, when the tissue is far from the tumor, a weak converging force is received, and the difference vector will indicate small movement. Here, for the image interpreting doctor, it is easier to find the convergence with respect to the tumor by interpreting a cross-sectional image of a cross-section where the amount of movement of the tissue is large, and the image interpreting doctor will highly likely be able to determine that the tumor is an adenocarcinoma without error.

Therefore, in the first embodiment, the cross-sectional image generating unit 1007 generates a cross-sectional image of the predetermined cross-section 422a in which the movement amount of the tissue is large, so that the image interpreting doctor can use the generated cross-sectional image for image interpretation. According to the example of FIG. 16, two difference vectors (1600_1 and 1600_2) are included in the cross-sectional image 1600 of the cross-section 412a. On the other hand, the number of difference vectors included in the cross-sectional image 422 of the cross-section 422a is seven (422_1 to 422_7), and the vector size is larger.

Therefore, by enlarging and displaying the cross-sectional image 422 of the cross-section 422a instead of the image 1400 (=the cross-sectional image 1600 of the cross-section 412a) of the corresponding area 402, the image interpreting doctor can easily find the convergence with respect to the tumor. As a result, the image interpreting doctor can determine that the tumor is an adenocarcinoma without error.

Figure 17:
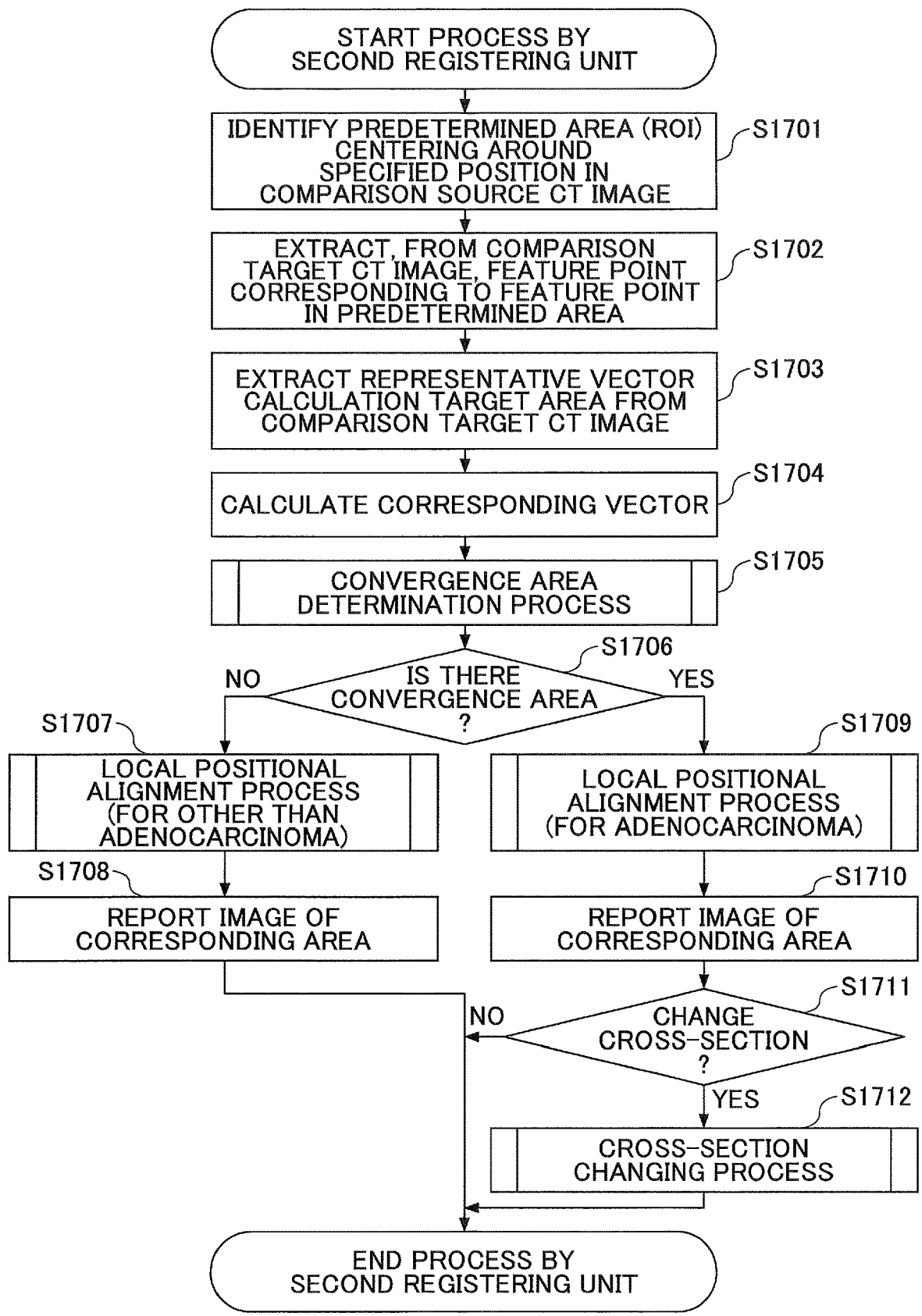
FIG. 17 is a flowchart of a process executed by the second registering unit.

Next, a flow of a process executed by the second registering unit 142 will be described. FIG. 17 is a flowchart of a process executed by the second registering unit 142.

In step S1701, the area identifying unit 1001 identifies the predetermined area 401 centered on the position of the tumor portion F specified by the image interpreting doctor in the comparison source CT image.

In step S1702, the corresponding vector calculating unit 1002 extracts feature points from the predetermined area 401 in the comparison source CT image identified by the area identifying unit 1001. Furthermore, the corresponding vector calculating unit 1002 searches for and extracts each feature point in the comparison target CT image corresponding to each of the extracted feature points.

In step S1703, the convergence area determining unit 1003 extracts an area including the feature points extracted from the comparison target CT image, as the representative vector calculation target area 800.

In step S1704, based on the differences between the positions of the respective feature points extracted from the comparison source CT image and the positions of the respective feature points in the comparison target CT image corresponding to the feature points of the comparison source CT image, the corresponding vector calculating unit 1002 calculates corresponding vectors.

In step S1705, based on the calculated corresponding vectors, the convergence area determining unit 1003 determines whether the convergence area 702 is included in the representative vector calculation target area 800. Furthermore, when the convergence area determining unit 1003 determines that the convergence area 702 is included, the convergence area determining unit 1003 calculates a boundary position between the normal area 701 and the convergence area 702. A detailed flowchart of the convergence area determination process in step S1705 will be described later.

In step S1706, the representative vector calculating unit 1004 determines the presence or absence of the convergence area 702 based on the result of the convergence area determination process (step S1705). In step S1706, when the representative vector calculating unit 1004 determines that the convergence area 702 is not included ("NO" in step S1706), the process proceeds to step S1707. In step S1707, the representative vector calculating unit 1004 and the positional aligning unit 1005 perform a local positional alignment process according to a tumor other than an adenocarcinoma. Note that a detailed flowchart of the local positional alignment process (for other than adenocarcinoma) in step S1707 will be described later.

In step S1708, the representative vector calculating unit 1004 reports the image subjected to local positional alignment as the image of the corresponding area 402, to the display control unit 143. Accordingly, the image subjected to local positional alignment is enlarged and displayed on the enlarged display screen.

Conversely, in step S1706, when the representative vector calculating unit 1004 determines that the convergence area 702 is included ("YES" in step S1706), the process proceeds to step S1709. In step S1709, the representative vector calculating unit 1004 and the positional aligning unit 1005 perform a local positional alignment process according to an adenocarcinoma. Note that a detailed flowchart of the local positional alignment process (for adenocarcinoma) in step S1709 will be described later.

In step S1710, the representative vector calculating unit 1004 reports the image 1400 on which the local positional alignment has been performed, as the image of the corresponding area 402, to the display control unit 143. Accordingly, the image 1400 on which the local positional alignment has been performed in step S1709, is enlarged and displayed on the enlarged display screen.

In step S1711, the partial image extracting unit 1006 determines whether a cross-section change instruction (or both a cross-section change instruction and a difference vector display instruction), with respect to the image 1400 enlarged and displayed on the enlarged display screen, has been input.

In step S1711, when the partial image extracting unit 1006 determines that a cross-section change instruction has not been input ("NO" in step S1711), the process by the second registering unit 142 is ended. Conversely, in step S1711, when the partial image extracting unit 1006 determines that the cross-section change instruction has been input ("YES" in step S1711), the process proceeds to step S1712.

In step S1712, the partial image extracting unit 1006 instructs the units from the area identifying unit 1001 to the positional aligning unit 1005, to execute the process from step S1701 to steps S1706 and S1709 for the CT images of the respective layers before and after the comparison target CT image.

Furthermore, the partial image extracting unit 1006 extracts the partial images 1511 to 1517, from the images of the comparison target CT image and the corresponding areas (corresponding areas 1501 to 1503, 402, and 1505 to 1507) included in the CT images of the layers before and after the comparison target CT image. Furthermore, the cross-sectional image generating unit 1007 generates a cross-sectional image (the cross-sectional image 422 of the cross-section 422a) based on the extracted partial images 1511 to 1517, and reports the cross-sectional image to the display control unit 143. Accordingly, the cross-sectional image (the cross-sectional image 422 of the cross-section 422a) obtained by performing the cross-section changing process is enlarged and displayed on the enlarged display screen, instead of the image 1400 (=the cross-sectional image 1600 of the cross-section 412a) for which local positional alignment has been performed.

Furthermore, the partial image extracting unit 1006 extracts a partial image from a predetermined area included in the comparison source CT image and the CT image of each layer before and after the comparison source CT image. Furthermore, the cross-sectional image generating unit 1007 generates a cross-sectional image based on the extracted partial images, and reports the cross-sectional image to the display control unit 143. Accordingly, the cross-sectional image obtained by performing the cross-section changing process in step S1712 is enlarged and displayed on the enlarged display screen, instead of the image 600 of the predetermined area 401. Note that a detailed flowchart of the cross-section changing process in step S1712 will be described later.

Figure 18:
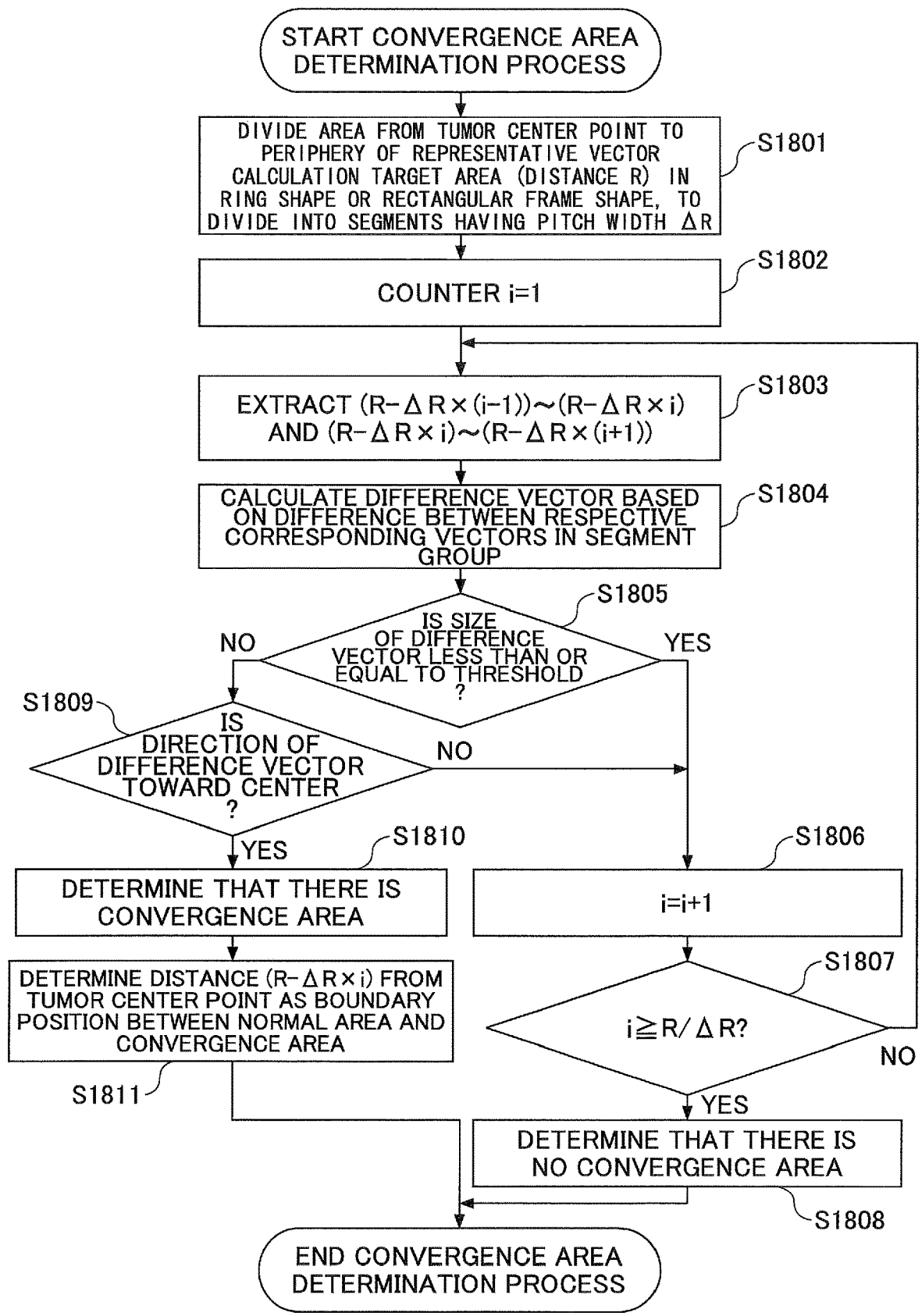
FIG. 18 is a flowchart of the convergence area determination process.

Next, details of the convergence area determination process (step S1705) will be described. FIG. 18 is a flowchart of the convergence area determination process.

In step S1801, the convergence area determining unit 1003 divides the area from the center (the center point O of the tumor) to the periphery of the representative vector calculation target area 800, into segments having a pitch width $\Delta R$, in a circular ring shape or a rectangular frame shape. In step S1802, the convergence area determining unit 1003 assigns 1 in the counter i.

In step S1803, the convergence area determining unit 1003 extracts a segment group in the range of $(R-\Delta R \times (i-1))$ to $(R-\Delta R \times i)$ and a segment group in the range of $(R-\Delta R \times i)$ to $(R-\Delta R \times (i+1))$ positioned on the inside of the aforementioned segment group (on the side close to the tumor).

In step S1804, the convergence area determining unit 1003 calculates a difference between adjacent corresponding vectors in the extracted respective segment groups, and obtains difference vectors.

In step S1805, the convergence area determining unit 1003 determines whether the size of the difference vector is less than or equal to a threshold value. In step S1805, when the convergence area determining unit 1003 determines that the size is less than or equal to a threshold value ("YES" in step S1805), the process proceeds to step S1806, and the counter i is incremented.

In step S1807, the convergence area determining unit 1003 determines whether i≥R/ΔR is satisfied. When the convergence area determining unit 1003 determines that i≥R/ΔR is not satisfied ("NO" in step S1807), the convergence area determining unit 1003 determines that there is a segment group further inside (the side closer to the tumor), and the process returns to step S1803.

Conversely, in step S1807, when the convergence area determining unit 1003 determines that i≥R/ΔR is satisfied ("YES" in step S1807), the convergence area determining unit 1003 determines that difference vectors have been calculated for all of the segment groups, and proceeds to step S1808.

In step S1808, the convergence area determining unit 1003 determines that the convergence area 702 is not included in the representative vector calculation target area 800, and ends the convergence area determination process.

Conversely, in step S1805, when the convergence area determining unit 1003 determines that the size of the difference vector is greater than a threshold value ("NO" in step S1805), the process proceeds to step S1809. In step S1809, the convergence area determining unit 1003 determines whether the direction of the difference vector is directed toward the center of the representative vector calculation target area 800.

In step S1809, when the convergence area determining unit 1003 determines that the direction of the difference vector is not directed toward the center ("NO" in step S1809), the process proceeds to step S1806. Conversely, in step S1809, when the convergence area determining unit 1003 determines that the direction of the difference vector is directed toward the center ("YES" in step S1809), the process proceeds to step S1810.

In step S1810, the convergence area determining unit 1003 determines that the convergence area 702 is included in the representative vector calculation target area 800, and proceeds to step S1811. In step S1811, the convergence area determining unit 1003 determines the position where the distance is (R−ΔR×i) from the center of the representative vector calculation target area 800, as the boundary position between the normal area 701 and the convergence area 702, and ends the convergence area determination process.

Figure 19:
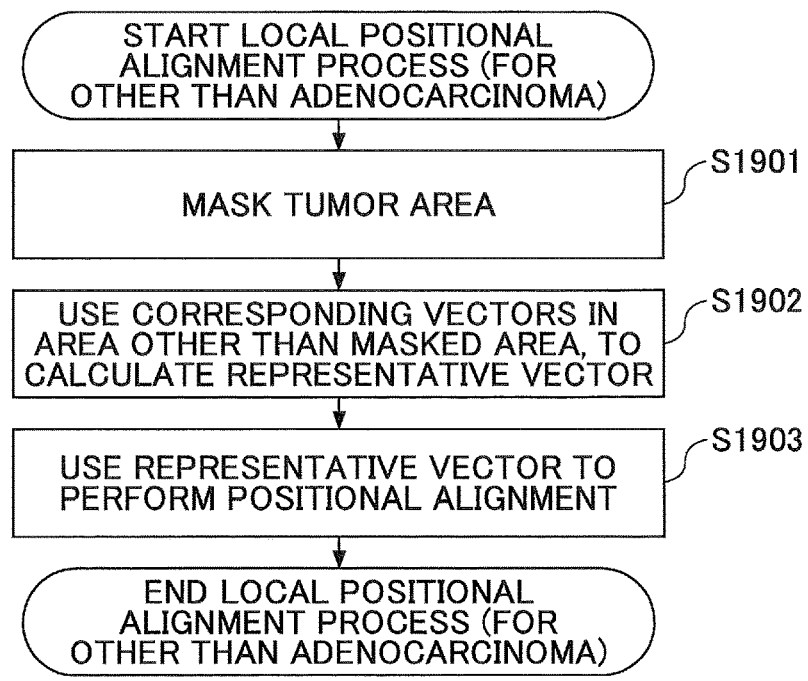
FIG. 19 is a flowchart of a local positional alignment process (for other than adenocarcinoma)

Next, details of the local positional alignment process (for other than adenocarcinoma) in step S1707 will be described. FIG. 19 is a flowchart of a local positional alignment process (for other than adenocarcinoma).

In step S1901, the representative vector calculating unit 1004 masks the tumor area 703 in the representative vector calculation target area 800.

In step S1902, the representative vector calculating unit 1004 calculates a representative vector by using corresponding vectors in areas other than the tumor area 703 masked in step S1901, among the corresponding vectors included in the representative vector calculation target area 800.

In step S1903, the positional aligning unit 1005 extracts an image of the corresponding area 402 corresponding to the predetermined area 401, from the comparison target CT image, by using the calculated representative vector. Accordingly, it is possible to extract an image subjected to local positional alignment.

Figure 20:
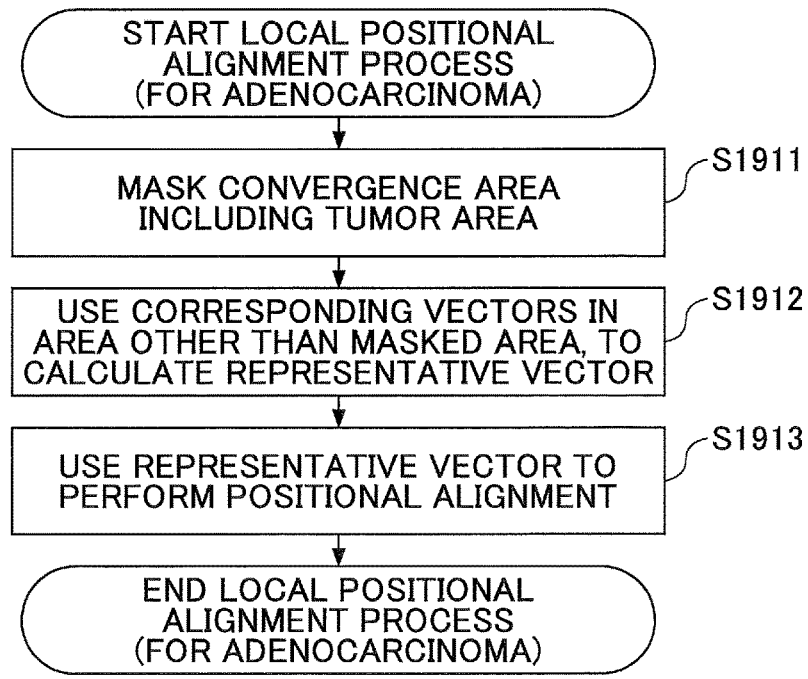
FIG. 20 is a flowchart of a local positional alignment process (for adenocarcinoma)

Next, details of the local positional alignment process (for adenocarcinoma) in step S1709 will be described. FIG. 20 is a flowchart of a local positional alignment process (for adenocarcinoma). In step S1911, the representative vector calculating unit 1004 masks the convergence area 702 including the tumor area 703 in the representative vector calculation target area 800.

In step S1912, the representative vector calculating unit 1004 calculates a representative vector by using corresponding vectors in areas other than the convergence area 702 masked in step S1911, among the corresponding vectors included in the representative vector calculation target area 800.

In step S1913, the positional aligning unit 1005 extracts the image 1400 of the corresponding area 402 corresponding to the predetermined area 401, from the comparison target CT image, by using the calculated representative vector. Thus, it is possible to extract an image subjected to local positional alignment.

Figure 21:
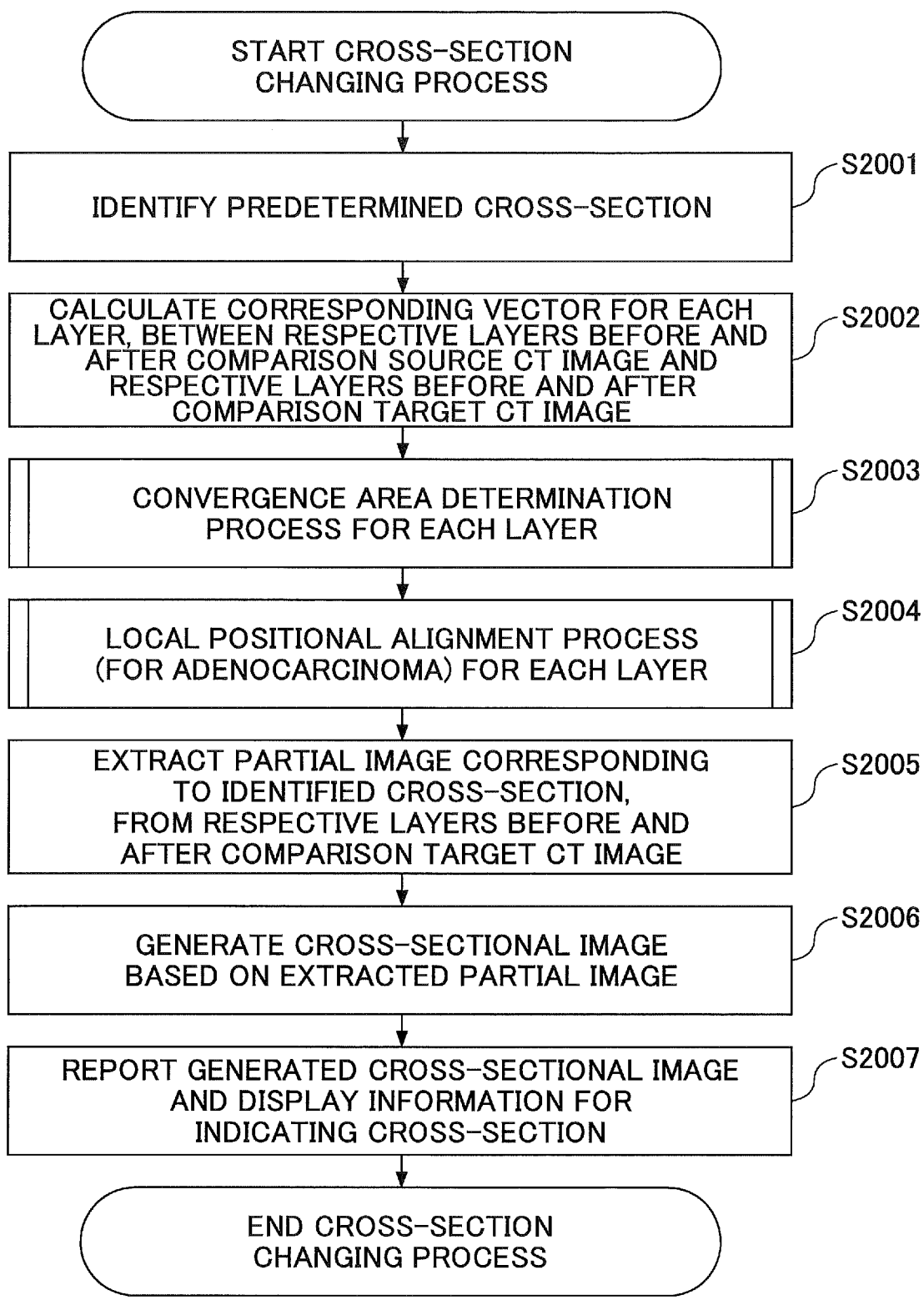
FIG. 21 is a first flowchart of the cross-section changing process.

Next, the cross-section changing process (step S1712) will be described in detail. FIG. 21 is a flowchart of the cross-section changing process.

In step S2001, the partial image extracting unit 1006 identifies a predetermined cross-section. The predetermined cross-section is a planar surface including a tumor and is the cross-section 412a obtained by rotating the cross-section by a predetermined cross-sectional angle around a predetermined axis (cross-sectional direction) with respect to the reference cross-section. The predetermined cross-section may be determined in advance or may be instructed by the image interpreting doctor.

In step S2002, the partial image extracting unit 1006 instructs the area identifying unit 1001 and the corresponding vector calculating unit 1002, to calculate the corresponding vectors for each layer, between the layers before and after the comparison source CT image and the layers before and after the comparison target CT image. Accordingly, the area identifying unit 1001 and the corresponding vector calculating unit 1002 calculate corresponding vectors for each layer, between the layers before and after the comparison source CT image and the layers before and after the comparison target CT image.

In step S2003, the partial image extracting unit 1006 instructs the convergence area determining unit 1003 to execute a convergence area determination process for each layer. Accordingly, the convergence area determining unit 1003 executes the convergence area determination process for each layer. Note that the contents of the convergence area determination process executed for each layer are the same as the convergence area determination process described with reference to FIG. 18, so detailed descriptions will be omitted here.

In step S2004, the partial image extracting unit 1006 instructs the representative vector calculating unit 1004 and the positional aligning unit 1005 to execute a local positional alignment process for each layer. Accordingly, the representative vector calculating unit 1004 and the positional aligning unit 1005 execute a local positional alignment process for each layer. Note that the contents of the local positional alignment process executed for each layer have already been described with reference to FIG. 20, so detailed descriptions thereof will be omitted here.

In step S2005, the partial image extracting unit 1006 acquires images (the images of the corresponding areas 1501 to 1503, 402, and 1505 to 1507) on which the local positional alignment has been performed in step S2004. Furthermore, the partial image extracting unit 1006 extracts the partial images 1511 to 1517 corresponding to the cross-section 422a identified in step S2001, from the acquired respective images of the corresponding areas 1501 to 1503, 402, and 1505 to 1507.

In step S2006, the cross-sectional image generating unit 1007 generates a cross-sectional image (the cross-sectional image 422 of the cross-section 422a) based on the partial images 1511 to 1517 extracted in step S2005. Note that when a difference vector display instruction has been input, the differential vectors included in the respective partial images extracted in step S2005 are also acquired and superimposed on the cross-sectional image 422.

In step S2007, the cross-sectional image generating unit 1007 reports, to the display control unit 143, the generated cross-sectional image 422 and the display information 432 for indicating the cross-section 422*a* used for generating the cross-sectional image 422.

Note that FIG. 21 is a flowchart of a case where the cross-section changing process is performed on the image 1400 of the corresponding area 402; the same process is applicable to the case of performing the cross-section changing process on the image 600 of the predetermined area 401. Note that when performing the cross-section changing process on the image 600 of the predetermined area 401, steps S2005 to S2007 in the flowchart illustrated in FIG. 21 are executed, upon replacing "comparison target CT image" with "comparison source CT image" in step S2005.

As is apparent from the above description, in the first embodiment, when the position of the tumor portion F is specified by the image interpreting doctor in the comparison source CT image, the image of the predetermined area 401 is enlarged and displayed. Furthermore, local positional alignment is performed based on the image of the predetermined area 401, thereby extracting the image of the corresponding area 402 from the comparison target CT image and enlarging and displaying the extracted image.

Accordingly, the image interpreting doctor can easily recognize the corresponding areas between the CT images included in groups of cross-sectional images captured at different time periods, and the image interpreting doctor can also perform appropriate image interpretation with respect to the tumor.

Furthermore, in the first embodiment, when an instruction to change the cross-section is given from the image interpreting doctor, partial images according to the new cross-section are extracted from the images of the corresponding areas included in the comparison target CT image and the layers before and after the comparison target CT image. Furthermore, difference vectors (information indicating the state of convergence of tissues surrounding the tumor) included in the extracted partial images are extracted. Furthermore, the generated cross-sectional image (the generated cross-sectional image and difference vector, in the case where there is an instruction to display the difference vector) is enlarged and displayed.

This makes it possible to display the tumor and the state of convergence on the cross-section where convergence with respect to the tumor is more apparent, and the image interpreting doctor can easily find the convergence with respect to the tumor and determine that the tumor is an adenocarcinoma. That is, according to the first embodiment, it is possible to support the image interpreting doctor to determine whether the tumor is an adenocarcinoma.

Second Embodiment

In the first embodiment, the cross-sectional image generating apparatus 120 generates and displays a cross-sectional image of a predetermined cross-section or a cross-section instructed by an image interpreting doctor. However, in the second embodiment, cross-sectional images of various cross-sections are generated, and based on the difference vector (information indicating a structural change) included in each cross-sectional image, an evaluation value indicating the degree of structural change (degree of convergence with respect to the tumor) is calculated. Then, the cross-sectional image having the highest evaluation value is enlarged and displayed on the enlarged display screen. This makes it possible to display the tumor and the state of convergence on a cross-section where convergence with respect to the tumor appears most, among the various cross-sections. Hereinafter, the second embodiment will be described focusing on differences from the first embodiment.

First, a specific example of contents of processes by the partial image extracting unit 1006 according to the second embodiment will be described. FIGS. 22A through 23B are diagrams illustrating contents of processes by the partial image extracting unit 1006 according to the second embodiment.

Figure 22B:
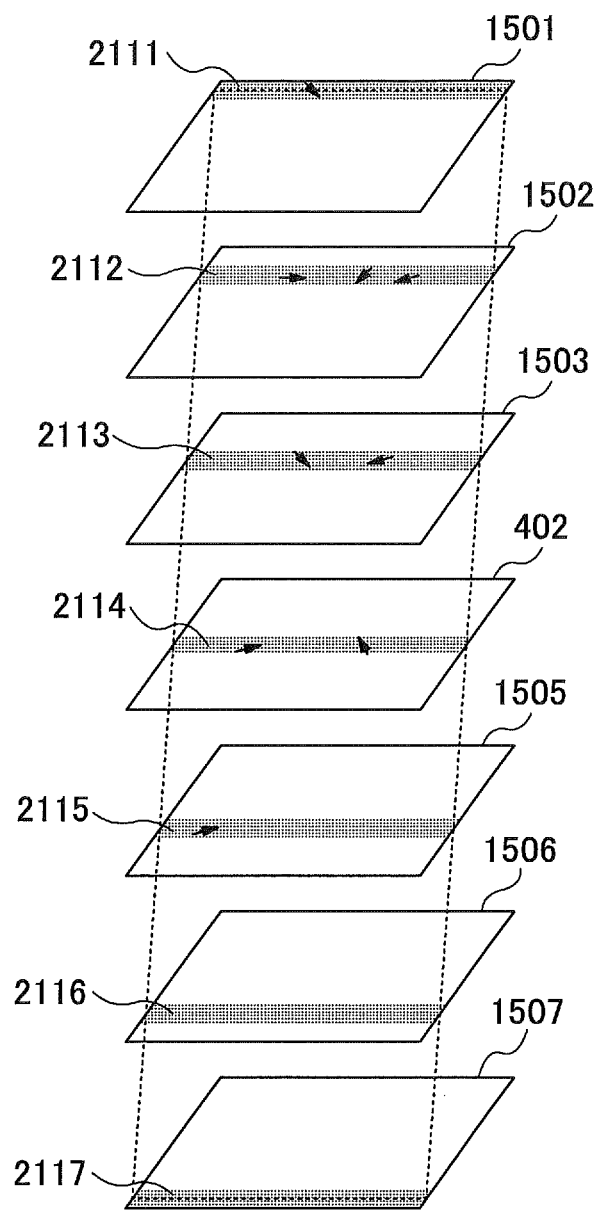
FIGS. 22A and 22B are diagrams illustrating contents of processes by the partial image extracting unit according to a second embodiment.
Figure 22A:
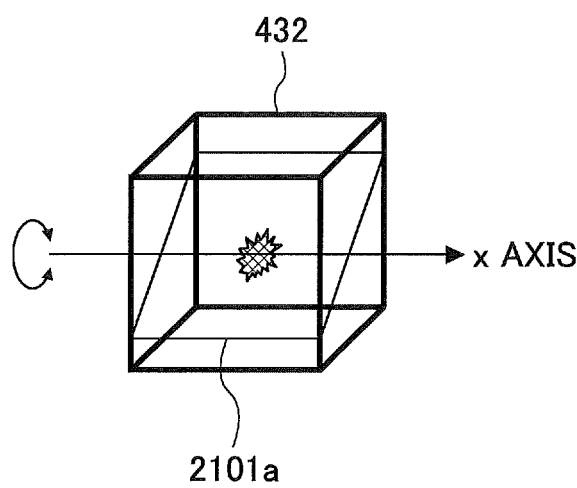

As illustrated in FIGS. 22A and 22B, the partial image extracting unit 1006 according to the second embodiment extracts partial images corresponding to a cross-section 2101*a* around the x axis, in addition to the partial images corresponding to the cross-section 422*a* around the y axis.

Specifically, the partial image extracting unit 1006 extracts partial images 2111 to 2117 corresponding to the cross-section 2101*a*, from the images of the corresponding areas 1501 to 1503, 402, and 1505 to 1507 included in the comparison target CT image and the CT images of the layers before and after the comparison target CT image.

Figure 23A:
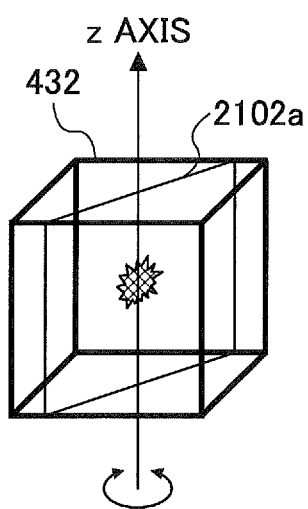
FIGS. 23A and 23B are diagrams illustrating contents of processes by the partial image extracting unit according to the second embodiment.
Figure 23B:
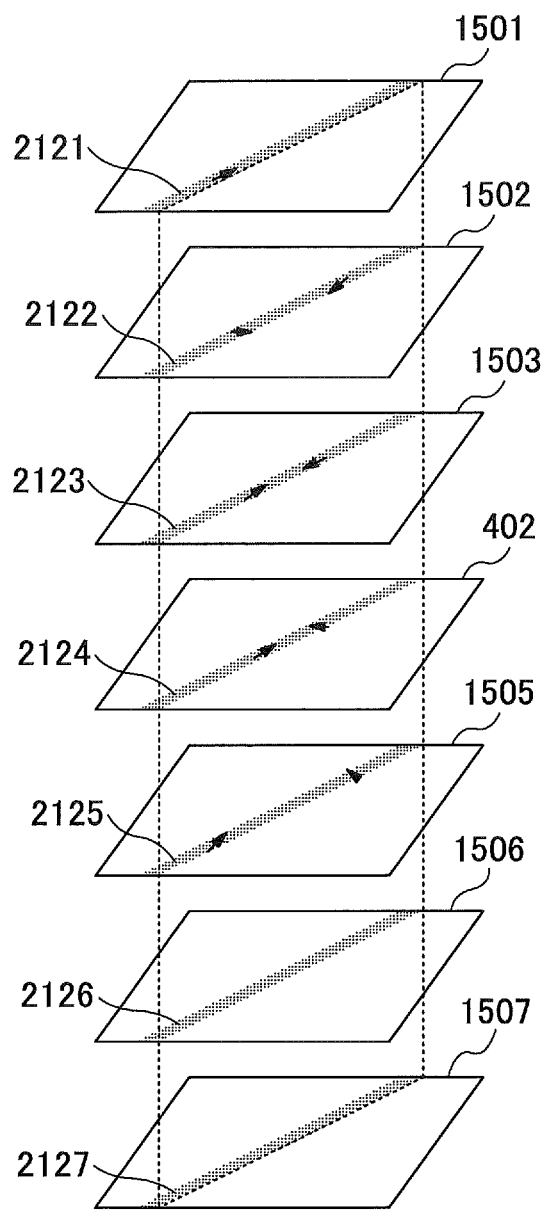

Furthermore, as illustrated in FIGS. 23A and 23B, the partial image extracting unit 1006 according to the second embodiment extracts partial images corresponding to a cross-section 2102*a* around the z axis.

Specifically, the partial image extracting unit 1006 extracts partial images 2121 to 2127 corresponding to the cross-section 2102*a*, from the images of the corresponding areas 1501 to 1503, 402, and 1505 to 1507 included in the comparison target CT image and the CT images of the layers before and after the comparison target CT image.

Next, a specific example of contents of processes by the cross-sectional image generating unit 1007 according to the second embodiment will be described. FIG. 24 is a diagram illustrating contents of processes by the cross-sectional image generating unit 1007 according to the second embodiment.

As illustrated in FIG. 24, the cross-sectional image generating unit 1007 according to the second embodiment generates cross-sectional images for the respective cross-sections obtained by changing the cross-sectional angle at a fixed pitch width around the x axis, the y axis, and the z axis. Furthermore, the cross-sectional image generating unit 1007 according to the second embodiment acquires difference vectors included in the respective generated cross-sectional images. Also, in each of the cross-sectional images, the cross-sectional image generating unit 1007 according to the second embodiment divides the radial area extending outward from the tumor center point O at fixed angular intervals, and extracts a different vector having the maximum vector length from the radial areas. Furthermore, the cross-sectional image generating unit 1007 according to the second embodiment obtains the sum of the evaluation values corresponding to the vector lengths of the respective difference vectors extracted from the respective radial areas, and calculates the total value of the evaluation values for each cross-sectional image.

The reason why radial areas and the largest difference vector are used as described above, is to make it easier for the image interpreting doctor to determine convergence. There are two requirements for an image interpreting doctor to easily determine convergence, namely, a tissue such as a blood vessel around the tumor is making a large movement, and the tissue is moving toward the center of the tumor. Among these, in order to address the former requirement (so that a higher evaluation value is obtained as the vector length is larger), the largest difference vector is used for calculating the evaluation value. Furthermore, in order to address the latter requirement (so that the evaluation value becomes high when vectors exist radially from all directions), only the largest difference vector in a given radial area is used for calculating the evaluation value.

The example of FIG. 24 (*i*) indicates that the cross-sectional image generating unit 1007 generates cross-sectional images 2210 to 2212 for the cross-sections 2210*a* to 2212*a* and that the differential vectors 2210_1 and 2210_2 are obtained in the cross-sectional image 2210. Furthermore, it is indicated that the cross-sectional image generating unit 1007 has determined the difference vectors 2210_1 and 2210_2 as the difference vectors having the maximum vector length in their respective radial areas. Furthermore, it is indicated that the evaluation values corresponding to the vector lengths of the difference vectors 2210_1 and 2210_2 have been calculated to be "0.8" and "0.9", respectively.

As a result, the cross-sectional image generating unit 1007 calculates the total value of the evaluation values of the cross-sectional image 2210 as "1.7". Note that in the example of FIG. 24 (*i*), the total value of the evaluation values of the cross-sectional image 2211 is further calculated as "1.1", and the total value of the evaluation values of the cross-sectional image 2212 is calculated as "2.4".

The example of FIG. 24 (*ii*) indicates that the cross-sectional image generating unit 1007 generates cross-sectional images 2220 to 2222 of the cross-sections 2220*a* to 2222*a* and that a difference 2220_1 is obtained in the cross-sectional image 2220. Furthermore, it is indicated that the cross-sectional image generating unit 1007 has determined the difference vector 2220_1 as a difference vector having the maximum vector length in its radial area, and has calculated the evaluation value corresponding to the vector length of the difference vector 2220_1 as "0.2".

As a result, the cross-sectional image generating unit 1007 calculates the total value of the evaluation values of the cross-sectional image 2220 as "0.2". Note that in the example of FIG. 24 (*ii*), the total value of the evaluation values of the cross-sectional image 2221 is further calculated as "0.1", and the total value of the evaluation values of the cross-sectional image 2222 is calculated as "0.5".

The example of FIG. 24 (*iii*) indicates that the cross-sectional image generating unit 1007 generates cross-sectional images 2230 to 2232 of the cross-sections 2230*a* to 2232*a* and that the difference vectors 2230_1 to 2230_6 are obtained in the cross-sectional image 2230. Furthermore, it is indicated that the cross-sectional image generating unit 1007 has determined the difference vectors 2230_2, 2230_3, 2230_4, 2230_5, and 2230_6 as the difference vectors having the maximum vector length in their respective radial areas. Furthermore, it is indicated that the cross-sectional image generating unit 1007 has calculated the evaluation values corresponding to the vector lengths of the respective difference vectors 2230_2, 2230_3, 2230_4, 2230_5, and 2230_6 as "0.5", "0.4", "0.1", "0.8" and "0.8", respectively.

As a result, the cross-sectional image generating unit 1007 calculates the total value of the evaluation values of the cross-sectional image 2230 as "2.7". Note that in the example of FIG. 24 (*iii*), the total value of the evaluation values of the cross-sectional image 2231 is further calculated as "2.2", and the total value of the evaluation values of the cross-sectional image 2232 is calculated as "2.4".

The cross-sectional image generating unit 1007 compares the total values of the evaluation values of the plurality of cross-sectional images 2210 to 2212, 2220 to 2222, and 2230 to 2232, and determines a cross-sectional image for which the total value of the evaluation values is the maximum. In the example of FIG. 24, it is determined that the total value (="2.7") of the evaluation values of the cross-sectional image 2230 is maximum.

Therefore, the cross-sectional image generating unit 1007 reports the cross-sectional image 2230 to the display control unit 143. Accordingly, the display control unit 143 can enlarge and display the cross-sectional image 2230 in which the convergence with respect to the tumor is most visible, on the enlarged display screen, among the various generated cross-sectional images.

Note that when a difference vector display instruction has been input, the cross-sectional image generating unit 1007 reports the difference vectors 2230_1 to 2230_6 included in the cross-sectional image 2230, to the display control unit 143. Accordingly, the display control unit 143 can enlarge and display the differential vector together with the cross-sectional image.

As described above, in the second embodiment, the cross-sectional image generating unit 1007 functions as an identifying unit for identifying a new cross-section different from the reference cross-section, based on the information (difference vector) indicating the structural change.

Figure 25:
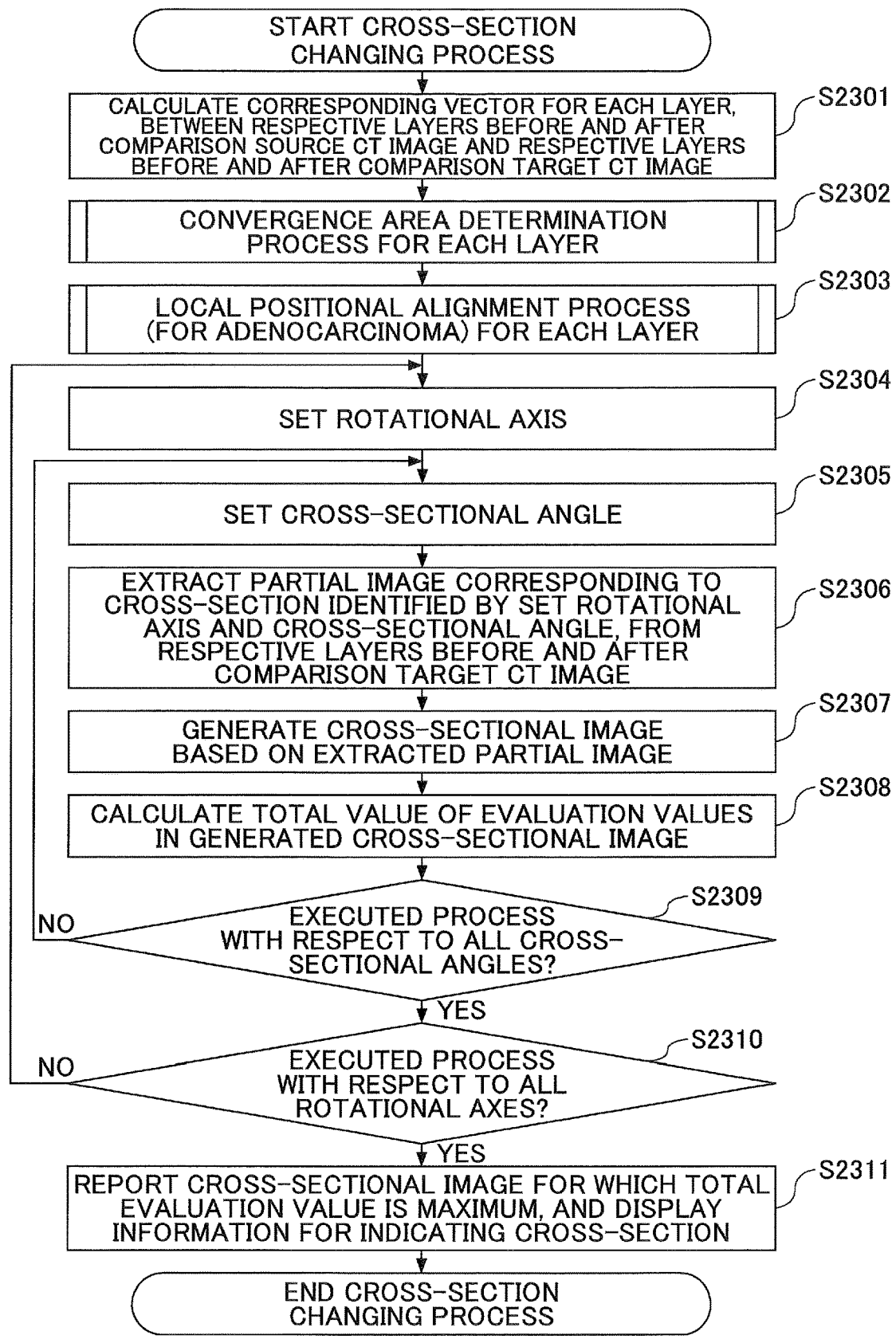
FIG. 25 is a second flowchart of the cross-section changing process.

Next, the details of the cross-section changing process (step S1712) according to the second embodiment will be described. FIG. 25 is a flowchart of the cross-section changing process. Note that steps S2301 to S2303 are the same as steps S2002 to S2004 of FIG. 21, and therefore, descriptions thereof are omitted here.

In step S2304, the partial image extracting unit 1006 sets a rotation axis for changing the cross-sectional angle by a fixed pitch width. It is assumed that the partial image extracting unit 1006 sets a rotation axis in an order of the x axis, the y axis, and the z axis. Here, it is assumed that the x axis is initially set as the rotation axis.

In step S2305, the partial image extracting unit 1006 sets the cross-sectional angle. In step S2306, the partial image extracting unit 1006 extracts partial images corresponding to the cross-section identified by the set rotation axis and cross-sectional angle, from the comparison target CT image and the layers before and after the comparison target CT image.

In step S2307, the cross-sectional image generating unit 1007 generates a cross-sectional image based on the extracted partial images. For example, the cross-sectional image generating unit 1007 generates a cross-sectional image 2210.

In step S2308, the cross-sectional image generating unit 1007 calculates the total value of the evaluation values in the generated cross-sectional image. For example, the cross-sectional image generating unit 1007 calculates "1.7" as the total value of the evaluation values in the cross-sectional image 2210.

In step S2309, the cross-sectional image generating unit 1007 determines whether a cross-sectional image has been generated for all cross-sectional angles. In step S2309, when the cross-sectional image generating unit 1007 determines that there is a cross-sectional angle for which a cross-sectional image has not been generated ("NO" in step S2309), the process returns to step S2305, the cross-sectional angle is changed by a fixed pitch width, and step S2306 to step S2308 are executed.

Conversely, in step S2309, when the cross-sectional image generating unit 1007 determines that a cross-sectional image has been generated for all cross-sectional angles ("YES" in step S2309), the process proceeds to step S2310.

In step S2310, the partial image extracting unit 1006 determines whether all the rotation axes have been set. In step S2310, when the partial image extracting unit 1006 determines that there is a rotation axis that has not been set ("NO" in step S2310), the process proceeds to step S2304. In this case, since only the x axis has been set, the process returns to step S2304, the y axis is set, and then the processes of steps S2305 to S2309 are executed. Furthermore, after setting the z axis, the processes from steps S2305 to S2309 are executed.

In step S2310, when the partial image extracting unit 1006 determines that all of the rotation axes have been set ("YES" in step S2310), the process proceeds to step S2311. In step S2311, the cross-sectional image generating unit 1007 compares the total values of the evaluation values of the generated cross-sectional images, and identifies the cross-sectional image for which the maximum total value of evaluation values has been calculated. Furthermore, the cross-sectional image generating unit 1007 reports, to the display control unit 143, the identified cross-sectional image and the display information 432 for indicating the cross-section used for generating the identified cross-sectional image.

As is apparent from the above description, in the second embodiment, cross-sectional images of various cross-sections are generated and the degree of structural change (the degree of convergence with respect to the tumor) is evaluated based on the difference vector included in each cross-sectional image. Furthermore, in the second embodiment, the cross-sectional image having the highest evaluation value is identified, and the identified cross-sectional image is enlarged and displayed.

Thus, according to the second embodiment, it is possible to display the tumor and the state of convergence on the cross-section where convergence with respect to the tumor appears most, among various cross-sections, and the image interpreting doctor can find the convergence with respect to the tumor and easily determine that the tumor is an adenocarcinoma. That is, according to the second embodiment, it is possible to support the image interpreting doctor to determine whether the tumor is an adenocarcinoma.

Third Embodiment

In the first and second embodiments, when there is an instruction to change the cross-section, a cross-sectional image of a cross-section having a planar surface including a tumor center point, is generated as an image to be displayed, instead of the image of the corresponding area 402. However, in the third embodiment, a cross-sectional image of a cross-section that is a curved surface including the tumor center point, is generated. The cross-section where convergence with respect to a tumor appears, is not limited to a planar surface, and the convergence with respect to a tumor may appear more visibly in a cross-sectional image of a cross-section that is a curved surface. Hereinafter, the third embodiment will be described focusing on differences from the first or second embodiment.

Figure 26C:
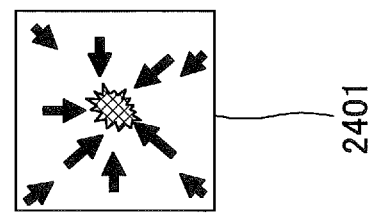
FIGS. 26A through 26C are diagrams illustrating contents of processes by the cross-sectional image generating unit according to a third embodiment.
Figure 26B:
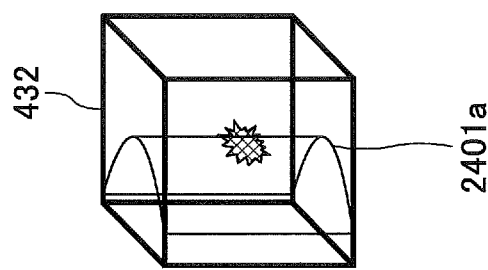
Figure 26A:
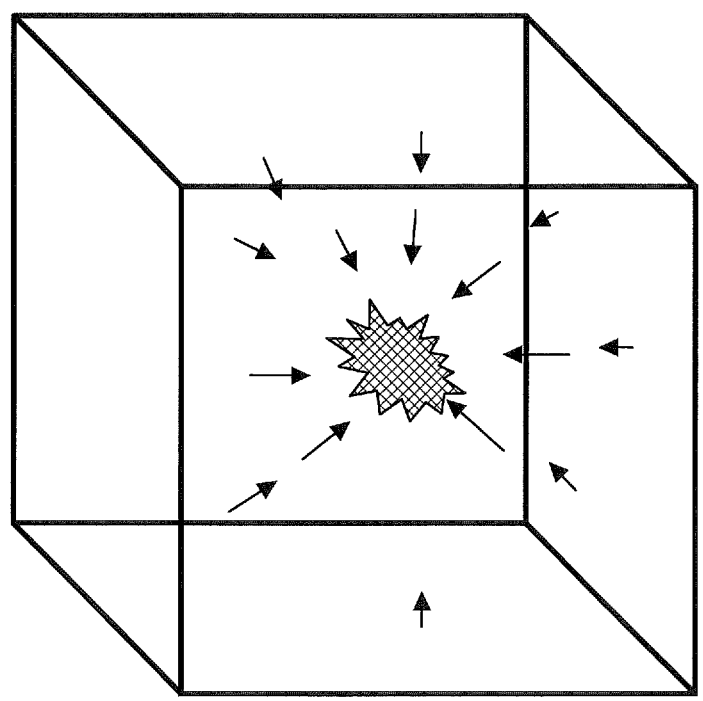

First, a specific example of contents of processes by the cross-sectional image generating unit 1007 according to the third embodiment will be described. FIGS. 26A through 26C are diagrams illustrating contents of processes by the cross-sectional image generating unit 1007 according to the third embodiment. As illustrated in FIG. 26A, among the surrounding tissues of the tumor, the area of the surrounding tissue moving toward the tumor, is irregular. Therefore, there is a high possibility that convergence with respect to a tumor is more apparent in a cross-section that is a curved surface including the tumor center point, rather than a planar surface including the tumor center point.

FIG. 26B illustrates an example of a curved surface 2401a including the tumor center point. FIG. 26C illustrates a cross-sectional image 2401 of the curved surface 2401a. As illustrated in FIG. 26C, the number of difference vectors included in the cross-sectional image 2401 of the curved surface 2401a is larger than the number of difference vectors included in any of cross-sectional images 2210 to 2212, 2220 to 2222, and 2230 to 2232 of a planar surface. Furthermore, the vector length of each difference vector is long. That is, it can be said that convergence with respect to the tumor is more apparent in a cross-sectional image of a curved surface.

Figure 27:
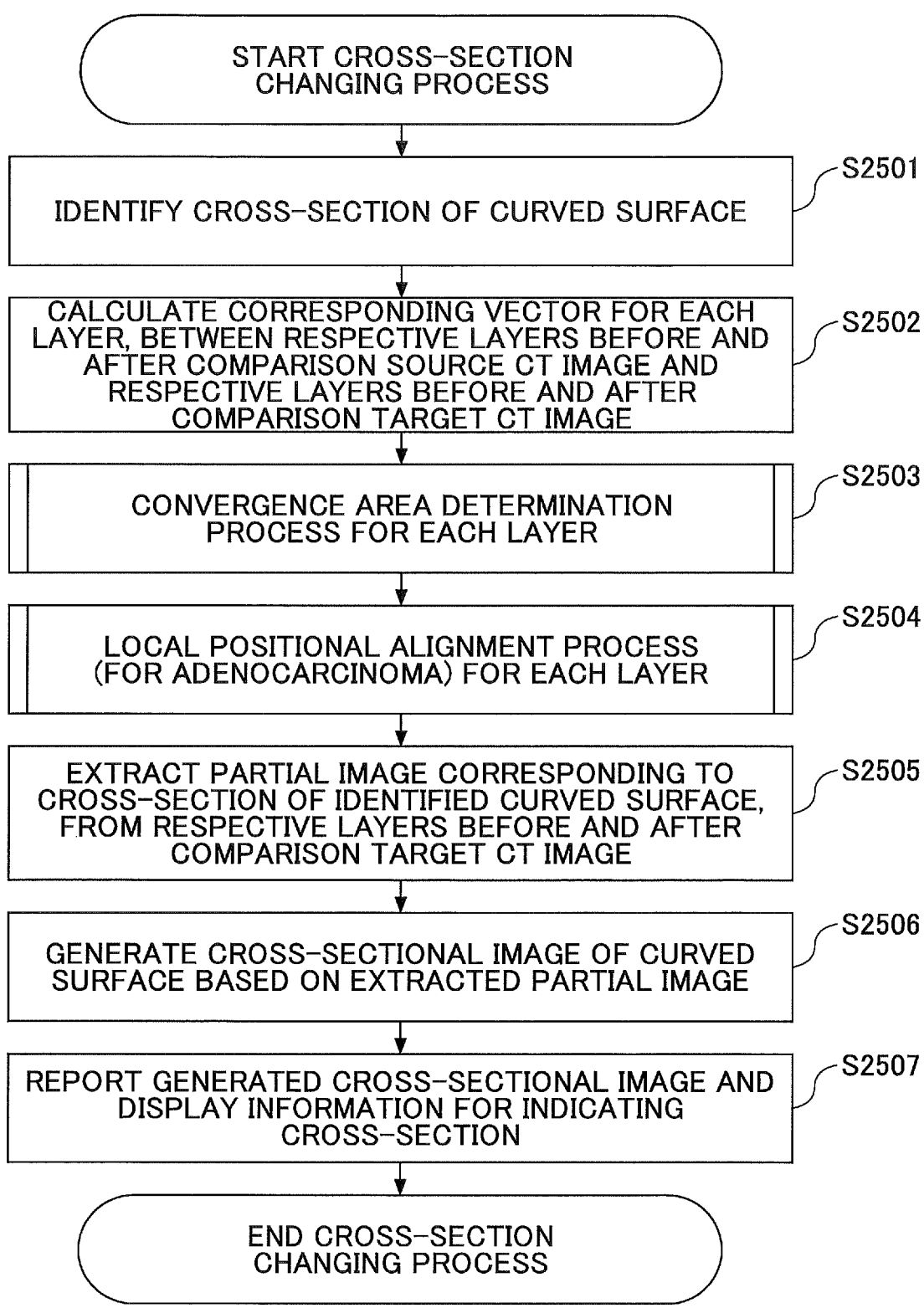
FIG. 27 is a third flowchart of the cross-section changing process.

Next, the cross-section changing process (step S1712) according to the third embodiment will be described in detail. FIG. 27 is a flowchart of the cross-section changing process. Note that steps S2501 to S2504 are the same as steps S2001 to S2004 in FIG. 21, and therefore descriptions thereof are omitted here. However, in step S2501, the partial image extracting unit 1006 identifies a curved surface by using, for example, a least-squares method, etc. Alternatively, the partial image extracting unit 1006 may identify a curved surface by using a Bezier curve.

In step S2505, the partial image extracting unit 1006 extracts partial images corresponding to the curved surface 2401a including the tumor center point of the comparison target CT image.

In step S2506, the cross-sectional image generating unit 1007 generates the cross-sectional image 2401 having the curved surface 2401a as a cross-section, based on the partial images extracted in step S2505. Note that when a difference vector display instruction has been input, the difference vectors included in the partial images extracted in step S2505 are also acquired and superimposed on the cross-sectional image 2401.

In step S2507, the cross-sectional image generating unit 1007 reports, to the display control unit 143, the cross-sectional image 2401 in which the generated curved surface is the cross-section, and the display information for indicating the curved surface 2401a used for generating the cross-sectional image 2401.

As described above, in the third embodiment, when there is an instruction to change the cross-section, a cross-sectional image whose cross-section is a curved surface including the tumor center point, is generated as an image to be displayed, instead of the image of the corresponding area 402. This makes it possible to display the tumor and the state of convergence on the cross-section where convergence with respect to the tumor is more apparent, and accordingly, the image interpreting doctor can find convergence with respect to the tumor and easily determine that the tumor is an adenocarcinoma. That is, according to the third embodiment, it is possible to support the image interpreting doctor to determine whether the tumor is an adenocarcinoma.

OTHER EMBODIMENTS

In the third embodiment, one cross-sectional image having a curved surface determined in advance as the cross-section is generated; however, similar to the second embodiment, it is also possible to generate cross-sectional images based on a plurality of curved surfaces, and select one cross-sectional image based on the total values of evaluation values calculated for the respective cross-sectional images.

Alternatively, by extracting partial images by selecting the partial image having the highest evaluation value from the surrounding partial images at each point directed outward from the tumor center point, and joining the extracted partial images, a cross-sectional image having a curved surface as the cross-section may be generated.

Furthermore, in the second embodiment, among a plurality of cross-sectional images, the cross-sectional image having the largest total value of evaluation values is enlarged and displayed on the enlarged display screen. However, the cross-sectional image to be enlarged and displayed on the enlarged display screen is not limited to one, and a plurality of cross-sectional images may be switched and enlarged and displayed according to instructions from the image interpreting doctor. In this case, the plurality of cross-sectional images to be switched and enlarged and displayed may be limited to, for example, the cross-sectional images having top ranking total values of evaluation values (for example, the top three cross-sectional images).

Note that the present invention is not limited to the configurations described in the above embodiments, such as combinations with other elements, etc. With respect to these points, variations may be made within a scope not deviating from the gist of the present invention, and the present invention may be appropriately defined according to the application form.

According to an aspect of the embodiments, a tumor and a convergence state are displayed on a cross-section where the convergence with respect to the tumor is appearing, and therefore it is possible to support an image interpreting doctor to determine whether the tumor is an adenocarcinoma.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable recording medium storing an image interpretation support program that causes a computer to execute a process, the process comprising:
    generating first data indicating a first internal structure of a predetermined object, based on a first cross-sectional image group acquired with respect to a reference cross-section of the predetermined object;
    detecting a structural change of the first internal structure from a second internal structure of the predetermined object, based on second data indicating the second internal structure and the generated first data indicating the first internal structure, the second data being generated based on a second cross-sectional image group acquired at a past time with respect to the reference cross-section of the predetermined object;
    identifying a new cross-section of the predetermined object different in a cross-sectional direction or a cross-sectional angle from the reference cross-section in response to receiving a cross-section changing instruction sent in view of the detected structural change;
    generating a cross-sectional image of the new cross-section of the predetermined object by using partial images extracted from first cross-sectional images of the first cross-sectional image group; and
    displaying the cross-sectional image of the new cross-section together with first information indicating the detected structural change.

2. The non-transitory computer-readable recording medium according to claim 1, the process further comprising:
    identifying a plurality of new cross-sections with respect to the predetermined object;
    generating a cross-sectional image of the predetermined object with respect to each of the plurality of new cross-sections, based on the first cross-sectional image group; and
    displaying a first cross-sectional image selected from the generated cross-sectional images.

3. The non-transitory computer-readable recording medium according to claim 1, the process further comprising:
    identifying a plurality of new cross-sections with respect to the predetermined object;
    generating a cross-sectional image of the predetermined object with respect to each of the plurality of new cross-sections, based on the first cross-sectional image group;
    calculating an evaluation value indicating a degree of the structural change based on the first information indicating the structural change, detected from the generated cross-sectional images; and
    displaying a first cross-sectional image selected by using the calculated evaluation value.

4. The non-transitory computer-readable recording medium according to claim 1, the process further comprising:
    displaying the generated cross-sectional image together with second information indicating the new cross-section identified for generating the cross-sectional image.

5. The non-transitory computer-readable recording medium according to claim 1, wherein the new cross-section with respect to the predetermined object is a planar surface or a curved surface including a tumor area included in the first data indicating the first internal structure.

6. The non-transitory computer-readable recording medium according to claim 1, wherein the first information indicating the structural change is a vector indicating a positional variation of a surrounding tissue based on a change in a tumor.

7. The non-transitory computer-readable recording medium according to claim 1, wherein
    the second data indicating the second internal structure is an image of a predetermined area including a tumor, and
    the first data indicating the first internal structure is an image of an area including a feature point corresponding to a feature point included in the image of the predetermined area.

8. A cross-sectional image generating apparatus comprising:
    a processor configured to execute a process including
    generating first data indicating a first internal structure of a predetermined object, based on a first cross-sectional image group acquired with respect to a reference cross-section of the predetermined object;

detecting a structural change of the first internal structure from a second internal structure of the predetermined object, based on second data indicating the second internal structure and the generated first data indicating the first internal structure, the second data being generated based on a second cross-sectional image group acquired at a past time with respect to the reference cross-section of the predetermined object;

identifying a new cross-section of the predetermined object different in a cross-sectional direction or a cross-sectional angle from the reference cross-section in response to receiving a cross-section changing instruction sent in view of the detected structural change;

generating a cross-sectional image of the new cross-section of the predetermined object by using partial images extracted from first cross-sectional images of the first cross-sectional image group; and displaying the cross-sectional image of the new cross-section together with first information indicating the detected structural change.

9. A cross-sectional image generating method executed by a computer, the cross-sectional image generating method comprising:

generating first data indicating a first internal structure of a predetermined object, based on a first cross-sectional image group acquired with respect to a reference cross-section of the predetermined object;

detecting a structural change of the first internal structure from a second internal structure of the predetermined object, based on second data indicating the second internal structure and the generated first data indicating the first internal structure, the second data being generated based on a second cross-sectional image group acquired at a past time with respect to the reference cross-section of the predetermined object;

identifying a new cross-section of the predetermined object different in a cross-sectional direction or a cross-sectional angle from the reference cross-section in response to receiving a cross-section changing instruction sent in view of the detected structural change;

generating a cross-sectional image of the new cross-section of the predetermined object by using partial images extracted from first cross-sectional images of the first cross-sectional image group; and displaying the cross-sectional image of the new cross-section together with first information indicating the detected structural change.

\* \* \* \* \*